United States Patent
De La Huerga

(10) Patent No.: US 7,061,831 B2
(45) Date of Patent: Jun. 13, 2006

(54) PRODUCT LABELING METHOD AND APPARATUS

(76) Inventor: Carlos De La Huerga, 9190 N. Upper River Rd., Milwaukee, WI (US) 53217

( * ) Notice: Subject to any disclaimer, the term of this patent is extended or adjusted under 35 U.S.C. 154(b) by 632 days.

(21) Appl. No.: 09/833,258

(22) Filed: Apr. 12, 2001

(65) Prior Publication Data

US 2001/0017817 A1    Aug. 30, 2001

Related U.S. Application Data

(63) Continuation-in-part of application No. 09/185,137, filed on Nov. 3, 1998, now Pat. No. 6,259,654, which is a continuation-in-part of application No. 09/168,783, filed on Oct. 8, 1998, which is a continuation-in-part of application No. 08/832,613, filed on Mar. 28, 1997, now Pat. No. 5,852,590, application No. 09/833,258, which is a continuation-in-part of application No. 10/627,987, filed on Jul. 28, 2000, and a continuation-in-part of application No. 09/168,783, filed on Oct. 8, 1998.

(51) Int. Cl.
 *G04B 47/00*    (2006.01)
(52) U.S. Cl. ............................. 368/10; 221/2; 221/129
(58) Field of Classification Search ................. 368/10, 368/107–113; 221/2–3, 15; 340/309.4, 340/573.1; 702/177; 283/67–114, 117; 215/11.2; 705/2–3
See application file for complete search history.

(56) References Cited

U.S. PATENT DOCUMENTS

| | | |
|---|---|---|
| 3,227,127 A | 1/1966 | Gayle |
| 3,762,601 A | 10/1973 | McLaughlin |
| 4,207,992 A | 6/1980 | Brown |
| 4,360,125 A | 11/1982 | Martindale |
| 4,368,988 A | 1/1983 | Tahara et al. |
| 4,384,288 A | 5/1983 | Walton |
| 4,437,579 A | 3/1984 | Obland |
| 4,476,381 A * | 10/1984 | Rubin .................. 235/375 |
| 4,483,626 A | 11/1984 | Nobel |
| 4,504,153 A * | 3/1985 | Schollmeyer et al. ......... 368/10 |
| 4,526,474 A | 7/1985 | Simon |
| 4,546,901 A | 10/1985 | Buttarazzi |
| 4,573,606 A | 3/1986 | Lewis et al. |

(Continued)

FOREIGN PATENT DOCUMENTS

GB    2154344    9/1985

OTHER PUBLICATIONS

Paul Lavin, "Small but perfectly informed Will a Java Ring become the next must-have fashion accessory?" The Independent, London, Apr. 7, 1998.

(Continued)

*Primary Examiner*—Randy W. Gibson
*Assistant Examiner*—Thanh S. Phan
(74) *Attorney, Agent, or Firm*—Quarles & Brady LLP

(57) ABSTRACT

A method and apparatus for configuring indicating configurations for containers wherein at least a subset of indicating configurations include an enhanced indicating device such as an electronic storage device, the containers to include enhanced devices being a function of whether or not the end user uses an interacting device capable of receiving information from the enhanced devices, the method and system indicating whether or not standard or enhanced containers should be used for specific prescriptions or orders and, in some cases, automatically providing the correct container and specifying (i.e., printing and writing) information to the containers.

34 Claims, 12 Drawing Sheets

U.S. PATENT DOCUMENTS

| | | |
|---|---|---|
| 4,575,621 A | 3/1986 | Dreifus |
| 4,598,275 A | 7/1986 | Ross et al. |
| 4,616,316 A | 10/1986 | Hanpeter et al. |
| 4,617,557 A | 10/1986 | Gordon |
| 4,626,105 A | 12/1986 | Miller |
| 4,664,289 A | 5/1987 | Shimizu et al. |
| 4,674,651 A | 6/1987 | Scidmore et al. |
| 4,674,652 A | 6/1987 | Aten et al. |
| 4,694,284 A | 9/1987 | Leveille et al. |
| 4,695,954 A | 9/1987 | Rose et al. |
| 4,717,261 A | 1/1988 | Kita et al. |
| 4,725,997 A | 2/1988 | Urquhart et al. |
| 4,730,849 A | 3/1988 | Siegel |
| 4,732,411 A | 3/1988 | Siegel |
| 4,733,362 A | 3/1988 | Haraguchi |
| 4,733,797 A | 3/1988 | Haber |
| 4,785,969 A | 11/1988 | McLaughlin |
| 4,811,764 A | 3/1989 | McLaughlin |
| 4,817,050 A | 3/1989 | Komatsu et al. |
| 4,823,982 A | 4/1989 | Aten et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,857,713 A | 8/1989 | Brown |
| 4,857,716 A * | 8/1989 | Gombrich et al. .......... 235/375 |
| 4,885,571 A | 12/1989 | Pauley et al. |
| 4,898,578 A | 2/1990 | Rubalcaba, Jr. |
| 4,911,327 A * | 3/1990 | Shepherd et al. .............. 221/3 |
| 4,916,441 A | 4/1990 | Gombrich |
| 4,939,705 A | 7/1990 | Hamilton et al. |
| 4,952,928 A | 8/1990 | Carroll et al. |
| 4,953,745 A | 9/1990 | Rowlett, Jr. |
| 4,967,928 A | 11/1990 | Carter |
| 4,971,221 A * | 11/1990 | Urquhart et al. ................ 221/2 |
| 4,972,657 A * | 11/1990 | McKee ....................... 53/411 |
| 4,973,944 A | 11/1990 | Maletta |
| 4,978,335 A | 12/1990 | Arthur, III |
| 4,980,671 A | 12/1990 | McCurdy |
| 4,984,709 A | 1/1991 | Weinstein |
| 5,012,229 A | 4/1991 | Lennon et al. |
| 5,014,875 A | 5/1991 | McLaughlin et al. |
| 5,032,823 A | 7/1991 | Bower et al. |
| 5,047,948 A | 9/1991 | Turner |
| 5,048,870 A | 9/1991 | Mangini et al. |
| 5,071,168 A | 12/1991 | Shamos |
| 5,075,670 A | 12/1991 | Bower et al. |
| 5,088,056 A | 2/1992 | McIntosh et al. |
| 5,099,463 A | 3/1992 | Lloyd et al. |
| 5,104,374 A | 4/1992 | Bishko et al. |
| 5,115,223 A | 5/1992 | Moody |
| 5,161,199 A | 11/1992 | David |
| 5,166,498 A | 11/1992 | Neeley |
| 5,176,285 A | 1/1993 | Shaw |
| 5,181,189 A | 1/1993 | Hafner |
| 5,193,855 A | 3/1993 | Shamos |
| 5,202,929 A | 4/1993 | Lemelson |
| 5,204,670 A | 4/1993 | Stinton |
| 5,208,762 A | 5/1993 | Charhut et al. |
| 5,213,232 A * | 5/1993 | Kraft et al. ................. 221/277 |
| 5,233,571 A | 8/1993 | Wirtschafter |
| 5,256,157 A | 10/1993 | Samiotes et al. |
| 5,271,642 A * | 12/1993 | Jahier et al. ................... 283/81 |
| 5,272,318 A | 12/1993 | Gorman |
| 5,289,157 A * | 2/1994 | Rudick et al. ......... 340/309.15 |
| 5,313,439 A | 5/1994 | Albeck |
| 5,317,506 A | 5/1994 | Coutre et al. |
| 5,319,363 A | 6/1994 | Welch et al. |
| 5,319,711 A | 6/1994 | Servi |
| 5,337,919 A | 8/1994 | Spaulding et al. |
| 5,347,453 A * | 9/1994 | Maestre ......................... 705/2 |
| 5,348,061 A | 9/1994 | Riley et al. |
| 5,381,487 A | 1/1995 | Shamos |
| 5,392,952 A | 2/1995 | Bowden |
| 5,398,220 A | 3/1995 | Baker |
| 5,401,059 A | 3/1995 | Ferrario |
| 5,405,048 A | 4/1995 | Rogers et al. |
| 5,408,443 A * | 4/1995 | Weinberger ................... 368/10 |
| 5,408,655 A | 4/1995 | Oren et al. |
| 5,412,372 A | 5/1995 | Parkhurst et al. |
| 5,431,299 A | 7/1995 | Brewer et al. |
| 5,435,600 A * | 7/1995 | Griffiths et al. ................ 283/81 |
| 5,445,621 A | 8/1995 | Poli et al. |
| 5,455,851 A | 10/1995 | Chaco et al. |
| 5,460,294 A | 10/1995 | Williams |
| 5,472,113 A | 12/1995 | Shaw |
| 5,477,511 A | 12/1995 | Englehardt |
| 5,480,062 A | 1/1996 | Rogers et al. |
| 5,491,482 A | 2/1996 | Dingwall et al. |
| 5,491,774 A | 2/1996 | Norris et al. |
| 5,493,805 A | 2/1996 | Penuela et al. |
| 5,495,961 A * | 3/1996 | Maestre ......................... 221/3 |
| 5,499,626 A | 3/1996 | Willham et al. |
| 5,502,445 A | 3/1996 | Dingwall et al. |
| 5,502,944 A | 4/1996 | Kraft et al. |
| 5,504,474 A | 4/1996 | Libman et al. |
| 5,508,499 A | 4/1996 | Ferrario |
| 5,511,000 A | 4/1996 | Kaloi et al. |
| 5,512,879 A | 4/1996 | Stokes |
| 5,512,880 A | 4/1996 | Abrams et al. |
| 5,519,808 A | 5/1996 | Benton, Jr. et al. |
| 5,522,525 A | 6/1996 | McLaughlin et al. |
| 5,525,969 A | 6/1996 | LaDue |
| 5,527,289 A | 6/1996 | Foster et al. |
| 5,532,705 A | 7/1996 | Hama |
| 5,541,580 A | 7/1996 | Gerston et al. |
| 5,541,583 A | 7/1996 | Mandelbaum |
| 5,548,566 A | 8/1996 | Barker |
| 5,548,660 A | 8/1996 | Lemelson |
| 5,564,005 A | 10/1996 | Weber et al. |
| 5,593,267 A | 1/1997 | McDonald et al. |
| 5,594,786 A | 1/1997 | Chaco et al. |
| 5,602,963 A | 2/1997 | Bissonnette et al. |
| 5,609,268 A | 3/1997 | Shaw |
| 5,609,716 A | 3/1997 | Mosher, Jr. |
| 5,612,675 A | 3/1997 | Jennings et al. |
| 5,621,384 A | 4/1997 | Crimmins et al. |
| 5,623,242 A | 4/1997 | Dawson, Jr. et al. |
| 5,627,520 A | 5/1997 | Grubbs et al. |
| 5,629,981 A | 5/1997 | Nerlikar |
| 5,642,906 A | 7/1997 | Foote et al. |
| 5,643,212 A | 7/1997 | Coutre |
| 5,646,912 A | 7/1997 | Cousin |
| 5,650,766 A | 7/1997 | Burgmann |
| 5,659,741 A | 8/1997 | Eberhardt |
| 5,660,176 A | 8/1997 | Lliff |
| 5,678,925 A * | 10/1997 | Garmaise et al. ........... 374/157 |
| 5,681,285 A | 10/1997 | Ford et al. |
| 5,689,567 A | 11/1997 | Miyauchi |
| 5,713,485 A * | 2/1998 | Liff et al. ...................... 221/2 |
| 5,713,856 A | 2/1998 | Eggers et al. |
| RE35,743 E | 3/1998 | Pearson |
| 5,732,401 A | 3/1998 | Conway |
| 5,742,233 A | 4/1998 | Hoffman et al. |
| 5,745,366 A | 4/1998 | Higham et al. |
| 5,768,813 A | 6/1998 | Reboul et al. |
| 5,771,001 A | 6/1998 | Cobb |
| 5,772,635 A | 6/1998 | Dastur et al. |
| 5,781,442 A | 7/1998 | Engleson et al. |
| 5,782,805 A | 7/1998 | Meinzer et al. |
| 5,793,290 A | 8/1998 | Eagleson et al. |
| 5,802,015 A * | 9/1998 | Rothschild et al. ........... 368/10 |
| 5,826,217 A | 10/1998 | Lerner |
| 5,833,599 A | 11/1998 | Schrier et al. |

| | | |
|---|---|---|
| 5,839,836 A | 11/1998 | Yuyama et al. |
| 5,851,186 A | 12/1998 | Wood et al. |
| 5,852,590 A | 12/1998 | de la Huerga |
| 5,852,911 A | 12/1998 | Yuyama et al. |
| 5,855,395 A | 1/1999 | Foote et al. |
| 5,868,669 A | 2/1999 | Lliff |
| 5,877,675 A | 3/1999 | Rebstock et al. |
| 5,877,742 A | 3/1999 | Klink |
| 5,882,338 A | 3/1999 | Gray |
| 5,883,370 A | 3/1999 | Walker et al. |
| 5,883,576 A | 3/1999 | de la Huerga |
| 5,924,074 A | 7/1999 | Evans |
| 5,936,529 A | 8/1999 | Reisman et al. |
| 5,945,651 A | 8/1999 | Chorosinski et al. |
| 5,954,700 A | 9/1999 | Kovelman |
| 5,960,085 A | 9/1999 | de la Huerga |
| 5,970,388 A | 10/1999 | Will |
| 5,979,757 A | 11/1999 | Tracy et al. |
| 5,980,501 A | 11/1999 | Gray |
| 5,997,476 A | 12/1999 | Brown |
| 6,019,745 A | 2/2000 | Gray |
| 6,032,155 A | 2/2000 | de la Huerga |
| 6,036,231 A * | 3/2000 | Foote et al. .................. 283/67 |
| 6,070,148 A | 5/2000 | Mori et al. |
| 6,070,761 A | 6/2000 | Bloom et al. |
| 6,104,295 A | 8/2000 | Gaisser et al. |
| 6,110,152 A | 8/2000 | Kovelman |
| 6,140,936 A | 10/2000 | Armstrong |
| 6,144,303 A | 11/2000 | Federman |
| 6,169,707 B1 | 1/2001 | Newland |
| 6,219,587 B1 | 4/2001 | Ahlin et al. |
| 6,255,951 B1 | 7/2001 | de la Huerga |
| 6,259,654 B1 | 7/2001 | de la Huerga |
| 6,263,330 B1 | 7/2001 | Bessette |
| 6,283,761 B1 | 9/2001 | Joao |
| 6,294,999 B1 | 9/2001 | Yarin et al. |
| 6,317,390 B1 | 11/2001 | Cardoza |
| 6,317,648 B1 * | 11/2001 | Sleep et al. ................. 700/216 |
| 6,324,123 B1 | 11/2001 | Durso |
| 6,346,886 B1 | 2/2002 | de la Huerga |
| 6,877,658 B1 * | 4/2005 | Raistrick et al. ............ 235/385 |

OTHER PUBLICATIONS

"Medical alerty systems," The University of California Berkley Wellness Letter, vol. 7, No. 1, p. 1, Oct. 1990.

"Surgical patients carry records on wristband", USA Today, vol. 126, No. 2631, p. 7, Dec., 1997.

* cited by examiner

Sponsored Medications Profile Database

| Medications | Criteria | Functions | Duration | Sponsor | Rule # |
|---|---|---|---|---|---|
| A | None | All | UC | Company A | 001 |
| A | Med B | All | UC | Company A | 002 |
| A | Med B & X | 2, 4, 10 | UC | Company A | 003 |
| B | Med A | All | UC | Company A | 002 |
| B | Diagnosis B | 2, 4, 7 | 1/1/2001 - 1/1/2002 | Company B | 004 |
| C | Meds A & B | All | UC | Company A | 002 |
| C | Med D | All | UC | Company C | 006 |
| D | Question 1 YES = Meet Criteria | 2, 3 | UC | Company D | 005 |
| ⋮ | ⋮ | ⋮ | ⋮ | ⋮ | ⋮ |
| All | Meds A | All | UC | Company A | 001 |

Fig. 15

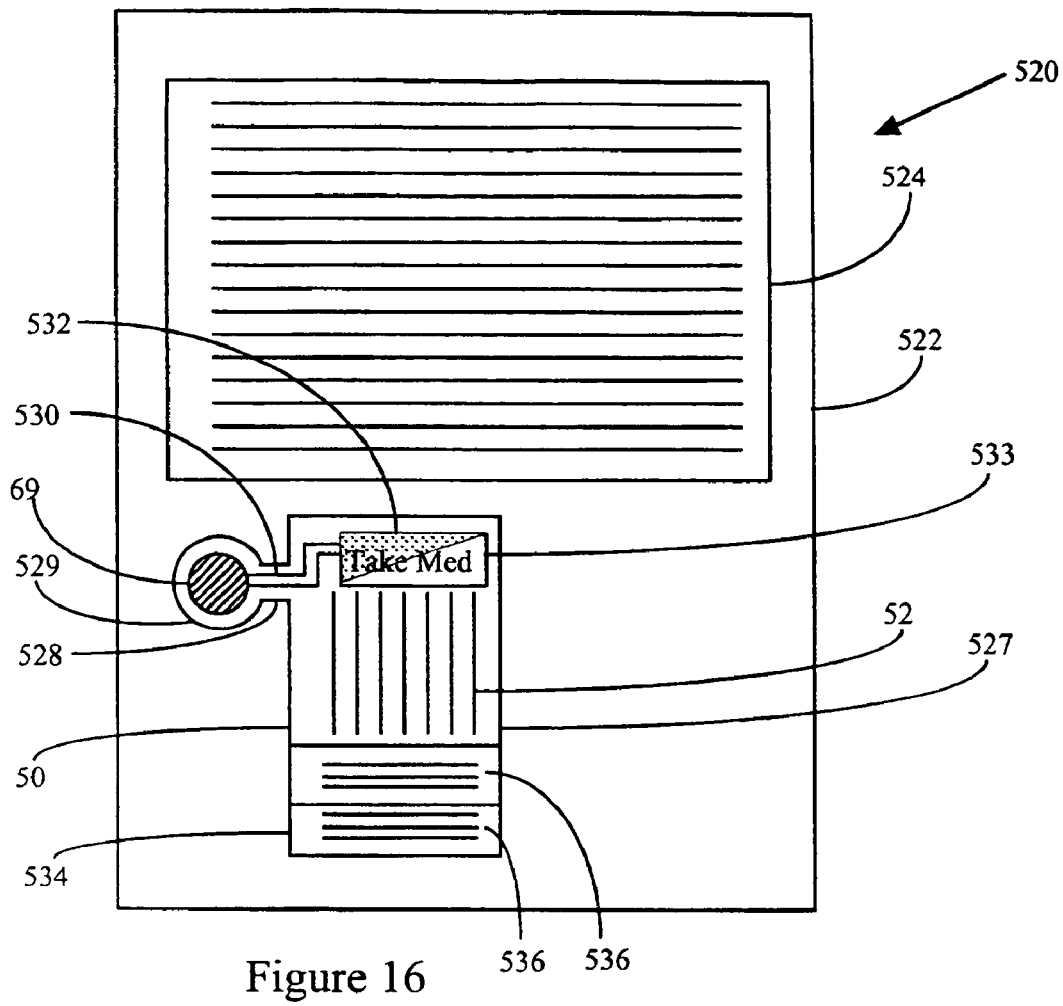
Figure 16
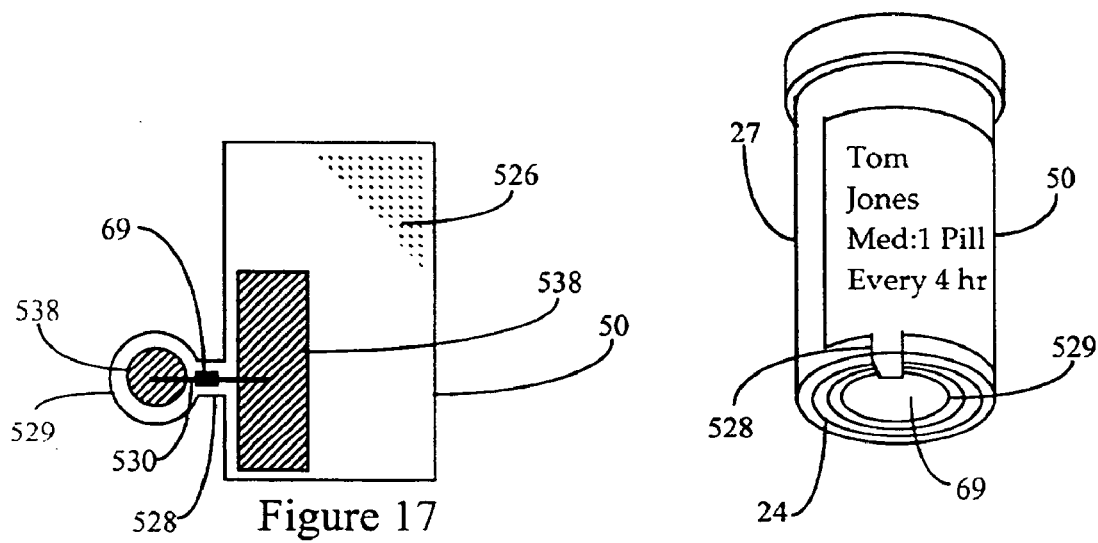
Figure 17
Figure 18

PRODUCT LABELING METHOD AND APPARATUS

CROSS-REFERENCE TO RELATED APPLICATIONS

This is a continuation in part of U.S. patent application Ser. No. 09/185,137 which was filed on Nov. 3, 1998 and is entitled "Multi-vial Medication Organizer and Dispenser" now U.S. Pat. No. 6,259,654 and which was a continuation-in-part of U.S. patent application Ser. No. 09/168,783 which was filed on Oct. 8, 1998 titled "Medication Dispensing Machine Cassette With Interactive Information Strip" which is a continuation-in-part of Ser. No. 08/832,613 filed Mar. 28, 1997 now U.S. Pat. No. 5,852,590 entitled "Interactive Label for Medication Containers and Dispensers" which issued on Dec. 22, 1998. This is also a continuation in part of U.S. patent application Ser. No. 10/627,987 which was filed on Jul. 28, 2000 and is entitled "Interactive Medication Container". In addition, this is a continuation in part of U.S. patent application Ser. No. 09/168,783 which was filed on Oct. 8, 1998 and which is entitled "Medication Dispensing Machine Cassette with Interactive Information Strip". Each of the above references are incorporated herein by reference.

STATEMENT REGARDING FEDERALLY SPONSORED RESEARCH OR DEVELOPMENT

Not applicable.

BACKGROUND OF THE INVENTION

The field of the invention is container labeling and more specifically labeling systems ensure that machine readable labels or devices correspond to human readable labels or the like.

With the widespread acceptance of electronic processors and machine-readable memories or labels, interactive electronic devices that can actually read information from memories and labels are becoming extremely common. For example, simple bar codes have been used for many years on grocery products to indicate the product type. In this case, upon checking out of a grocery store products are passed over a bar code reader which reads the bar code information to identify the product, correlates the product with a cost and adds the cost to a running cost total to be paid by a customer.

In addition to increasing efficiency, simple bar codes are advantageous because they are extremely inexpensive to produce. For example, simple bar codes are typically printed directly on an observable surface or on a label that is then attached to a container or other item identifying device (e.g., a wristband). Moreover, simple bar codes are usually used only to provide minimal information and therefore code-reading devices need not be very complex.

While simple bar codes have several advantages, unfortunately such simple codes have two important shortcomings. First, two limitations taken together restrict the amount of information that can be stored using a simple bar code. To this end, bar codes are relatively unattractive and therefore only small areas are reserved on package exterior surfaces to accommodate such codes. In addition, in order to be read using conventional bar code readers, code bars have to be at least a certain size. Thus, minimum bar size and maximum code area together limit the maximum amount of information storable via a simple bar code. For example, a typical simple code on a cereal box may only indicate cereal type and box volume (i.e., cereal quantity in the box).

Second, because of how bar codes are typically used, bar coded information is often limited to independently authenticatable and confirmable information types. For example, the end result of relying upon a cereal box bar code when checking out at a grocery store is to pay a specific price for the cereal within the box. For this reason it is important that, after a bar code is read, a consumer can independently compare the bar code information to known information. In the case of the cereal box this means that the consumer can compare the information read from the bar code to other information provided on the exterior surfaces of the cereal box to confirm that the information is consistent. Thus, the code and human readable information is redundant and comparable.

As another example, patient wristbands at medical facilities often include bar codes that can be used with a bar code reader to identify patients. In these cases the code readable patient identification can be independently legitimized and corroborated by asking a conscious and cognizant patient to confirm that the patient is in fact the patient identified by the band. Thus, the coded information and the known identity of the patient are redundant and comparable.

These two limitations combine to render simple bar codes essentially useless for some applications. For example, U.S. Pat. No. 5,852,590 titled "Interactive Label for Medication Containers and Dispensers" that was issued on Dec. 22, 1998 teaches several different embodiments of memory devices attached to external surfaces of medication containers where the devices are capable of storing a relatively larger amount of information when compared to simple bar codes. The memory devices may be, for example, relatively more complex multi-dimensional (e.g., two or three-dimensional) bar codes or dot matrices or RFID tags.

The above referenced application teaches that various types of redundant (i.e., information repeated in a human readable form on the container) and unique (i.e., information that is not repeated in human readable form on the container) information related to the medication to be stored in the containers can be stored on the memory devices. For example, a prescribing physician's identification, a primary physician's identification, a consumption regimen, contra-indication information, allergy information, re-ordering information, e-mail addresses of a primary physician and/or a prescribing physician, identification of the person to take the medication, patient physical characteristics, medication manufacturer's information, consumption rescheduling information, instructions for notifying a primary physician of a prescription, processor instructions for post-consumption queries regarding symptoms and instructions for functions to perform when specific symptoms occur, etc., can all be stored in the memory device.

The above referenced application also teaches processing devices that cooperate with the memory devices to facilitate various health related functions. For example, one health related function is to alert a device user whenever a prescription calls for medication consumption. Another function is to, when medication is removed from a container, update a quantity representative of the amount of medication in the container. One other function is to, when the quantity falls to a specified level and a medication can be refilled, automatically order the refill medication via a computer network (i.e., the Internet) or the like. Yet another function is to track mis-medication (i.e., when a medication was supposed to be consumed but was not or when a medication was consumed at a time that was not prescribed) and either notify the device user or a physician or indicate such mis-medication via a compiled report. Thus, clearly additional memory capabilities facilitate many useful and valuable functions.

While the present invention can be used in any of several different applications, in the interest of simplifying this explanation, the prior art and the present invention will be described in the context of the medical prescribing and pharmaceutical industry generally unless specifically indicated otherwise.

Unfortunately, as is often the case, additional functionality comes at a price. First, memory device readers constitute an added medication cost and therefore, while there are many advantages associated with such devices, some medication users will not be able to afford such memory readers. In addition, even if a medication user can afford a reader device, many users may not want the functionality that is facilitated by such readers. Indifference to such functionality will be particularly acute where a person only sporadically uses medication as in the case of a typical healthy adult. In either of these cases, the medication users will not have memory readers.

Second, in many cases the enhanced memory devices are relatively more expensive than simple bar codes. For example, an RFID tag includes a small processor, an electronic memory and a printed antenna, all of the components provided on a label or printed directly on the surface of a container. Multi-dimensional bar codes and dot matrices are sometimes subject to licensing fees and therefore are also relatively expensive. Thus, to minimize overall medication costs, enhanced memory devices should only be used in cases where a medication user has and employs a memory reader.

Third and, perhaps most importantly, as indicated above, much of the information that is useful to facilitate the additional functionality will not be redundant but instead will be unique and, for this reason there will be no way for a medication user to independently confirm that the information required to support intended functionality is actually provided on the memory device or, if provided, is correct. For example, a primary physician's e-mail address and notification instructions for warning the physician that a particular medication has been prescribed for a patient typically will not be provided in human readable form and therefore that information cannot be independently verified by a system user.

As another example, it may be the case that, with a specific medication, if dizziness occurs one hour after consumption, the prescription should be altered and/or an e-mail should be transmitted to the prescribing physician notifying the physician of the symptom. In this case, the memory information may include a query regarding dizziness, instructions to provide the query one hour after consumption, instructions to alter the prescription and/or transmit an e-mail to the physician if dizziness occurs and the physician's e-mail address. All of this information is important but nevertheless cannot be independently confirmed by a system user as the information would not be provided in a human readable format.

It might also be noted that even if such a laundry list of information were provided in a human readable format it is likely no one would take the time to compare the memory stored information and the human readable information to make sure that the information matched and was accurate.

While independent confirmation of information stored on an enhanced memory device is essentially impossible after a patient leaves a medical facility, unfortunately, negative consequences can result from incorrect information. For example, if a regimen prescribed for patient A is different than a regimen prescribed for patient B and patient A's regimen information is stored on a memory device attached to a medication container marked in human readable form for patient B, patient B will be alerted to take the medication in the container at incorrect consumption times (assuming the regimen's for patients A and B are different). As another example, if patient A's physician is notified of mis-medication instead of patient B's physician due to incorrect information on a memory device, the physician may either not recognize the patient identified in the message and therefore ignore the notice or may assume that an emergency has occurred. Many other sequences of inadvertent and problematic events are contemplated.

Fourth; the task of writing information to enhanced devices would be an additional burden. To this end, it is contemplated that the device readers will be programmable to perform many different functions and the different functions may require different information and that, for each medication there may be different information required to be written to the enhanced devices. Specifying all of this information each time a medication is to be dispensed would be extremely time consuming.

Fifth, even if the costs associated with enhanced devices are reduced to the point where such devices can be included on every container despite some container users not having reader devices, there will always be the problem of making sure that, for users of reader devices, information is provided on the enhanced devices. For example, assume a medication user does have a reader device and therefore wants to have a vial having an enhanced device that can be used by the reader to support certain functions. When a pharmacist dispenses medication to vial, labels the vial for the user and writes information to the enhanced device, there is no way to ensure that information intended for the enhanced device was actually written thereto. To an observer a vial with printed indicia will appear as a completely specified vial.

Thus, it would be advantageous to have a labeling system that could automatically determine when an enhanced memory device is desired for a medication container and that provides a container with such a device. In addition, it would be advantageous to have a system wherein a computer automatically confirms that the information on a machine-readable memory device is related to the printed and human readable information on a corresponding container.

BRIEF SUMMARY OF THE INVENTION

An exemplary embodiment of the present invention overcomes the above described problems is several ways including providing a system that automatically determines, based on some pre-stored criteria, whether or not a particular prescription should be filled in a container including an enhanced machine readable device. When an enhanced device is to be included on a container, the exemplary embodiment then performs one of several different protocols developed to ensure that correct information is written to the enhanced device (i.e., to ensure that the information stored on the device is the information corresponding to the specific prescription). Several embodiments facilitate automatic container configuration including provision of a label, an enhanced device and correlated information provided on each of the label and the enhanced device.

To this end one embodiment includes an apparatus for configuring an indicating configuration to be associated with a container wherein each indicating configuration includes an indicator and data stored thereon related to an order associated with the container and at least a sub-set of indicating configurations include an enhanced memory device and enhanced data stored thereon, an enhanced device being a device that cooperates with a data collector to gather information therefrom, at least one descriptor associated with each order that can be used to identify the indicating configuration and the data to be stored via the indicating configuration In this case the apparatus comprises a reader for reading each descriptor, a writer for writing data to enhanced devices and a processor linked to the reader for receiving each descriptor and using the descriptor to identify when enhanced data is associated with an order, the processor, when enhanced data is associated with an order, causing the writer to write enhanced data to an enhanced device and, when enhanced data is not associated with an order, causing another indicating function to be performed.

Thus, one object of the invention is to provide data for enhanced devices only when the eventual user of the container will use the enhanced device and some entity has agreed to fund the enhanced device. This system reduces over all costs by limiting use only to those who require an enhanced device. The funding entity may be the end user, a pharmacy, a pharmaceutical company, an insurance agency, etc.

This embodiment may further include a database correlating descriptors with associated data to be written to enhanced devices, the processor linked to the database and, when a descriptor is received, identifying by accessing the database and determining if enhanced data corresponds to the specific descriptor. The database may include an order queue including a plurality of orders, each order including a descriptor, the reader including a queue pointer that sequentially identifies each of the descriptors in the queue and provides the descriptors to the processor. Each container may be a medication container, each order may be a medication prescription for a particular medication user and the data may be data related to the medication to be stored in the container. In some embodiments the data is also a function of a medication user corresponding to the order.

In some embodiments at least a sub-set of the descriptors indicate that no data should be written to an enhanced device and wherein the another function includes disabling the writer when no data is to be written to an enhanced device.

The system may further include a container source controlled by the processor and providing containers having enhanced devices attached thereto. In some of these embodiments at least a sub-set of the descriptors indicate that no data should be written to an enhanced device and wherein the another function includes disabling the writer when no data is to be written to an enhanced device.

In yet other embodiments the container source includes an enhanced container source and a non-enhanced container source for providing enhanced and non-enhanced containers, respectively, and wherein, when a descriptor indicates that no data is to be written to an enhanced device, the another function includes causing the non-enhanced source to provide a non-enhanced container. In some cases the enhanced container source includes an enhanced device source and a device attacher, the attacher receiving non-enhanced containers and, when an enhanced container is required, attaching an enhanced device to a container to provide the enhanced container.

Thus, another object is to provide a system that automatically determines when an enhanced device should be included on a vial and then automatically provides the appropriate vial type (i.e., including or excluding an enhanced device). The system for providing enhanced devices and vials can vary as indicated above.

The processor may also use the descriptor to identify human readable indicia related to the order and the apparatus may further include an indicia printer for printing the indicia for inclusion on the container. The system may further include a label source for providing labels wherein the printer prints the indicia on the label. The system may also further include a label attacher for attaching the labels to the containers.

The enhanced devices may be attached to labels wherein the attacher attaches by attaching the labels to the container. The processor may also use the descriptor to identify human readable indicia related to the order and the apparatus may further include an indicia printer for printing the indicia on the label.

Yet another object is to provide a system wherein, in addition to providing enhanced devices and writing information to those devices, labels and human readable indicia can also automatically be provided for containers.

In other embodiments the system further includes a label source controlled by the processor and providing labels having enhanced devices attached thereto for inclusion on the containers. The another indicating function may include disabling the writer.

The label source may include an enhanced label source and a non-enhanced label source for providing enhanced labels including enhanced devices and non-enhanced labels, respectively. Here, when a descriptor indicates that no data is to be written to an enhanced device, the processor may cause the non-enhanced source to provide a non-enhanced label.

The enhanced label source may include an enhanced device source and a device attacher, the attacher receiving non-enhanced labels and, when an enhanced label is required, attaching an enhanced device to a label to provide the enhanced label.

The processor may also use the descriptor to identify human readable indicia to be included on the container wherein the indicia is related to the order, the apparatus further may include a label source and an indicia printer linked to the processor, the processor sequencing the indicia printing and data writing such that indicia and data corresponding to the same descriptor are provided on the same container. Each label may include an indicia surface and an attached enhanced device and the printer and writer may print and write the indicia and data corresponding to a single descriptor to the surface and device, respectively, at the same time.

Thus, one other object is to provide a system wherein the human readable indicia and the information stored on an enhanced device is correlated and corresponds to the same container content. To this end, by simultaneously writing and reading correlated information can be ensured.

Each of the writing and printing steps may be a specifying step and each of the indicia and data may be specifying information, a first of the specifying steps occurs before a second of the specifying steps, each printing and writing cycle may be a specifying cycle, for each descriptor, the first step occurs N specifying cycles prior to the second step and the processor may sequence the second step specifying information to be specified N cycles after the first step specifying information is specified. N in some embodiments is 1.

Thus, the invention contemplates other processes for ensuring that the printed indicia and stored information correspond such as by maintaining a specific sequence of steps and cycles between related printing and writing processes.

The system may further include a container source wherein the source provides containers with attached descriptors. The descriptor may include one of a bar code, a magnetic code, a Braille code and machine readable optical characters and the reader may include a matching one of a bar code reader, a magnetic code reader, a Braille code reader and a reader of the optical characters. The system may further include a database that correlates each descriptor with associated data to be written to enhanced devices, the processor linked to the database and, when a descriptor is received, identifying by accessing the database and locating the descriptor and associated data.

The system may further include an enhanced device source that may include the writer and that is linked to the processor wherein, the source providing an enhanced device to an apparatus user for attachment to the container ad after the processor identifies the data, the writer writing to the enhanced device.

The container may be a medication container, the data may be medication data and the data may include at least a sub-set of a patient ID, the medication type, prescribed dose, recommended dose, a prescribing physician's identification, primary physician's identification and instructions regarding a health safety function. The descriptors that indicate enhanced data may include the enhanced data and the processor may identify by reading the enhanced data.

Each enhanced device may be one of a RFID tag, an electronic memory, a magnetic tag, a multi-dimensional bar code and a dot matrix. The reader may include a hand held device that can be positioned in the vicinity of the descriptor and activated to read the descriptor. The hand held device may also comprise the writer that can be positioned in the vicinity of the enhanced device and activated to write to the enhanced device.

The processor may also use the descriptor to identify human readable indicia to be included on the container wherein the indicia may be related to the order, the apparatus further including an indicia printer linked to the processor, the another function including causing the indicia printer to print the human readable indicia for inclusion on the container.

Another embodiment includes an apparatus for providing medication containers at least a sub-set of which include enhanced devices wherein each enhanced device may include data related to an order associated with the container, the apparatus comprising an enhanced container source providing containers including attached enhanced devices, a non-enhanced container source, a processor equipped to control the sources, the processor determining when an enhanced container should be used to store the product and, when an enhanced container should be used, providing the enhanced container for storage and providing the data to be stored on the enhanced device and a writer for receiving the enhanced container and writing the data to the enhanced device.

The system may further comprise a database including an order queue including a plurality of orders, each order indicating if a container should include an enhanced device, the processor linked to the database and, for each order, using the order information to determine when an enhanced container should be provided. A sub-set of order recipients may use an interactive system that can read the enhanced devices wherein orders indicate that an enhanced container should be used by indicating that the order recipient uses such an interactive system.

The system may also be for providing human readable indicia on the containers, each indicia including data related to the product to be stored in the container, the apparatus further including an indicia provider for providing indicia to be associated with each of the containers, the processor linked to and controlling the indicia provider. The system may also include a labeler for providing a label for each of the containers, the indicia provider including a printer for printing the indicia on the labels. Here the labeler may apply the labels to the containers.

The indicia may include a descriptor that can be used by the processor to identify the data to be written to the enhanced device, the apparatus also including a reader for reading the descriptors wherein, after labeler applies the label to the container and the printer prints the indicia on the label, the reader reads the descriptor and provides the descriptor to the processor and the processor then uses the descriptor to identify the data to be written to the enhanced device. The container may be a medication container and the data may be medication data.

One other object is to use a descriptor that already exists in the form of a label to identify data to be stored on an enhanced device. In this way the trigger for information to be included on the enhanced device is the indicia on the label and therefore correlation is essentially assured.

Other embodiments of the invention include an apparatus for use with a container configuring system, the configuring system configuring containers at least a sub-set of which include enhanced devices for indicating data related to orders associated with the containers, the apparatus for providing an indication useable by the configuring system to provide properly configured containers, the apparatus comprising an input device for receiving an enhanced device indication and a recipient identification wherein the indication indicates that the associated recipient uses an interactive system that can read enhanced devices, a database for storing an enhanced device user list indicating recipients that use enhanced devices, an interface for specifying an order including at least a recipient identifier, a processor linked the database and receiving orders from the interface, determining if a recipient corresponding to the recipient identifier may be included in the enhanced device user list and, when a recipient may be included in the enhanced device user list, indicating an enhanced device user to the configuring system.

In some embodiments when the processor receives an order the processor stores the order in a database queue. Here, when the processor determines that a recipient is an enhanced device user, the processor may indicate the enhanced device user in the order prior to storing the order and then, during configuration, the processor may provide the indication to the configuring system. The processor may also determine if a user may be an enhanced device user during the configuration process.

Other embodiments include an indicator for use with containers and a container configuration system wherein the configuration system may be capable of providing at least a sub-set of containers that include enhanced memory devices where data related to an order associated with a container may be provided on the enhanced device, the indicator comprising a descriptor including a first segment including human readable indicia related to the product to be stored in the container and a second machine-readable segment useable to determine if an enhanced device including data should be provided on the container. Here the indicator may be one of a label and a part of the container on which the indicator may be included.

Yet other embodiments include an apparatus for identifying container types for storing product, the apparatus comprising an input device for specifying product information about the product to be stored in the container, the product information including label information to be provided on the container exterior, the label information requiring a specific surface area on the container exterior, a processor for determining, based at least in part on the required surface area, the container type and an output device for indicating the type of container to be used to store the product. Here the label information may include warnings to be provided on the container exterior, each warning requires a specific surface area on the container exterior, the total surface area required for the warnings on the container exterior may be a required area and the processor identifies the container type at least in part based on the required area. Also, here the information segment may include product type and quantity and the processor determines a required container volume based on product type and quantity and selecting the container type at least in part based on the required volume.

Yet one other object is to provide a system that can automatically identify the best container type to be used for storing a particular product as a function of the amount of space required on the exterior of the container to accommodate warnings and other necessary indications. For example, in the case of medication in a vial it may be necessary to include several warning labels in addition to medication information on the exterior of a vial. Some times the medication to be stored may only require a minimal volume while the warnings and other indications may require a much larger vial. In this case the larger vial would automatically be indicated.

The invention also includes several methods. One method is for use with a medication prescription system wherein at least a subset of medications may be stored in enhanced containers each of which include an enhanced device for storing data related to medications to be stored in the containers, the stored data useable by interactive devices that may obtain and use information from the enhanced devices to perform at least one health safety function, at least one sponsor sponsoring enhanced devices for storing at least one of the medications, the method for indicating container types as a function of sponsorship criteria. Here the method comprises the steps of providing sponsorship criteria indicating conditions under which the sponsor agrees to sponsor the at least one medication, receiving a prescription including prescription information for a user for the at least one medication, comparing circumstantial information including at least the prescription information to the sponsorship criteria, if the circumstantial information satisfies the sponsorship criteria, indicating that a container including an enhanced device should be used to store the medication and else, indicating that a container that does not include an enhanced device should be used to store the medication.

The means for providing sponsorship criteria may include providing a list of sponsored medications. The step of providing sponsorship criteria further may include the step of, for each sponsored medication in the list, providing a sponsored medication profile indicating, in addition to medication type, at least one other criteria required for sponsorship. The at least one other criteria may include simultaneous consumption of a medication in addition to the medication specified in the prescription. In the alternative, the at least one other criteria may include at least one of a medical condition and habit of the medication user for which the prescription was rendered, the method further including the step of indicating the at least one of the medical condition and habit of the user.

Thus, one other object is to facilitate a system whereby an medication sponsor can fund use of enhanced devices when certain criteria are met. While virtually any criteria may be supported exemplary criteria are described in more detail below.

There may be a plurality of different possible health safety functions that may be sponsored and the sponsor may sponsor only a subset of the possible functions. Here the step of providing sponsored medication profiles may include the step of, for each profile, providing an indication of which functions may be sponsored. The step of providing an indication of each sponsored function may include providing a pulse sequencing program to be stored on the enhanced device for performing at least part of each sponsored function. The method may further include the step of, when an enhanced container is indicated, providing an enhanced device and loading the sequencing program into the enhanced device.

In some embodiments the method further includes the step of loading other prescription information into the enhanced device. In addition the method may further include the step of printing at least a subset of the prescription information on the container in human readable indicia.

The sponsorship duration may be limited and the step of providing medication profiles further may include the step of, for each profile, providing an indication of sponsorship duration. The step of providing sponsored medication profiles further may include the step of, for each profile, indicating the sponsor. The step of indicating the sponsor further may include the step of providing information that can be used to bill the sponsor.

The step of providing sponsorship criteria further may include the step of providing an indication of the sponsor and billing information related to the sponsor and wherein the method further may include the step of, when an enhanced device may be indicated, generating a bill for the sponsor. The step of providing billing information may include providing a network address for the sponsor and the step of generating a bill further may include the step of transmitting billing information to the sponsor.

In several embodiments the step of providing sponsorship criteria may include indicating that at least two medications will be sponsored when criteria is met and providing a separate profile for each of the two medications, each profile associated with the criteria.

The step of providing sponsorship criteria may include indicating at least first and second prescribed medications, the method further may include the step of providing a user characteristics profile indicating all medications prescribed for the medication user and wherein the circumstantial information further may include the characteristics profile. The characteristics profile further may include a list of medication user conditions.

One other embodiment includes a method for configuring an indicating configuration to be associated with a container wherein each indicating configuration may include an indicator and data stored thereon related to an order associated with the container and at least a sub-set of indicating configurations include an enhanced memory device and enhanced data stored thereon, an enhanced device being a device that cooperates with a data collector to gather information therefrom, at least one descriptor associated with each order that can be used to identify the indicating configuration and the data to be stored via the indicating configuration, the method comprising reading each descriptor, receiving each descriptor and using the descriptor to identify when enhanced data may be associated with an order, when enhanced data may be associated with an order, writing enhanced data to an enhanced device and when enhanced data may be not associated with an order, causing another indicating function to be performed.

Here the method may further be for use with a database correlating descriptors with associated data to be written to enhanced devices such that when a descriptor is received, the method identifies by accessing the database and determining if enhanced data corresponds to the specific descriptor. Moreover, each container may be a medication container, each order may be a medication prescription for a particular medication user and the data may be data related to the medication to be stored in the container. The data may also be a function of a medication user corresponding to the order.

The system may include a writer to write data to enhanced devices, at least a sub-set of the descriptors indicate that no data should be written to an enhanced device and wherein the another function may include disabling the writer when no data may be to be written to an enhanced device.

In some embodiments the method further includes the steps of providing a container source controlled by the processor and providing containers having enhanced devices attached thereto. The system may include a writer to write data to enhanced devices, at least a sub-set of the descriptors indicate that no data should be written to an enhanced device and wherein the another function may include disabling the writer when no data may be to be written to an enhanced device.

The container source may include an enhanced container source and a non-enhanced container source for providing enhanced and non-enhanced containers, respectively. When a descriptor indicates that no data is to be written to an enhanced device, the another function may include causing the non-enhanced source to provide a non-enhanced container. The enhanced container source may include an enhanced device source and a device attacher, the attacher receiving non-enhanced containers and, when an enhanced container is required, attaching an enhanced device to a container to provide the enhanced container. The method may further include the step of using the descriptor to identify human readable indicia related to the order and printing the indicia for inclusion on the container.

The method may further include providing a label source for providing labels and the step of printing may include printing indicia on the label.

The method may in the alternative further include the steps of providing a label source for providing labels having enhanced devices attached thereto for inclusion on the containers. The step of providing a label source may further include providing an enhanced label source and a non-enhanced label source for providing enhanced labels including enhanced devices and non-enhanced labels, respectively, and wherein, when a descriptor indicates that no data may be to be written to an enhanced device, the method may include the step of causing the non-enhanced source to provide a non-enhanced label.

The method may further include the steps of using the descriptor to identify human readable indicia related to the product to be stored in the container and providing the indicia on the label.

The method may further including the steps of using the descriptor to identify human readable indicia to be included on the container wherein the indicia may be related to the order, providing a label and for printing the indicia and sequencing the indicia printing and data writing such that indicia and data corresponding to the same descriptor may be provided on the same container.

In several embodiments each label may include an indicia surface and an attached enhanced device and wherein the printing and writing steps include printing and writing the indicia and data corresponding to a single descriptor to the surface and device, respectively, at the same time.

In some embodiments each of the writing and printing steps may be a specifying step and each of the indicia and data may be specifying information, a first of the specifying steps occurs before a second of the specifying steps, each printing and writing cycle may be a specifying cycle, for each descriptor, the first step occurs N specifying cycles prior to the second step and the processor sequences the second step specifying information to be specified N cycles after the first step specifying information may be specified. N is sometimes 1.

In several embodiments the method further includes the step of providing a container source wherein the source provides containers with attached descriptors. The method may be used with a system including a database that correlates each descriptor with associated data to be written to enhanced devices, when a descriptor is received, the identifying step including identifying by accessing the database and locating the descriptor and associated data.

The method may further include the step of using the descriptor to identify human readable indicia to be included on the container wherein the indicia may be related to the order, the another function including printing the human readable indicia for inclusion on the container.

Yet another method is for providing medication containers at least a sub-set of which include enhanced devices wherein each enhanced device may include data related to an order associated with the container, the method comprising the steps of providing an enhanced container source providing containers including attached enhanced devices, providing a non-enhanced container source, determining when an enhanced container should be used to store the product and when an enhanced container should be used providing the enhanced container for storage and writing the data to the enhanced device.

Here the method may also be for providing human readable indicia on the containers, each indicia including data related to the product to be stored in the container, the method further including providing indicia to be associated with each of the containers. Moreover, the method may include printing the indicia on labels to be applied to the containers. The method may furthermore include applying the labels to the containers. The indicia may include a descriptor that can be used to identify the data to be written to the enhanced device, the method also including the steps of, after a label may be applied to a container and the indicia may be printed on the label, reading the descriptor and using the descriptor to identify the data to be written to the enhanced device.

On other method is for use with a container configuring system, the configuring system configuring containers at least a sub-set of which include enhanced devices for indicating data related to orders associated with the containers, the method for providing an indication useable by the configuring system to provide properly configured containers, the method comprising the steps of receiving an enhanced device indication and a recipient identification wherein the indication indicates that the associated recipient uses an interactive system that can read enhanced devices, storing an enhanced device user list indicating recipients that use enhanced devices, specifying an order including at least a recipient identifier and determining if a recipient corresponding to the recipient identifier may be included in the enhanced device user list and, when a recipient may be included in the enhanced device user list, indicating an enhanced device user to the configuring system.

A further method is for identifying container types for storing product, the method comprising the steps of specifying product information about the product to be stored in the container, the product information including label information to be provided on the container exterior, the label information requiring a specific surface area on the container exterior, determining, based at least in part on the required surface area, the container type and indicating the type of container to be used to store the product.

Here the label information may include warnings to be provided on the container exterior, each warning requires a specific surface area on the container exterior, the total surface area required for the warnings on the container exterior may be a required area and the step of identifying the container type may include identifying at least in part based on the required area.

Another apparatus is for use with a medication prescription system wherein at least a subset of medications may be stored in enhanced containers each of which include an enhanced device for storing data related to medications to be stored in the containers, the stored data useable by interactive devices that may obtain and use information from the enhanced devices to perform at least one health safety function, at least one sponsor sponsoring enhanced devices for storing at least one of the medications, the apparatus for indicating container types as a function of sponsorship criteria, the apparatus comprising a sponsored medication profile database indicating conditions under which the sponsor agrees to sponsor the at least one medication, an input device for receiving a prescription including prescription information for a user for the at least one medication and a processor performing a pulse sequencing program to perform the steps of receiving the prescription information and comparing circumstantial information including the prescription information to the sponsorship medication profiles if the circumstantial information satisfies the sponsorship criteria, indicating that a container including an enhanced device should be used to store the medication and else, indicating that a container that does not include an enhanced device should be used to store the medication. Here the sponsorship medication profile database may include a list of sponsored medications. Also, the sponsorship medication profile database further may include, for each medication in the list, a sponsored medication profile indicating, in addition to medication type, at least one other criteria required for sponsorship.

The at least one other criteria may include simultaneous consumption of a medication in addition to the medication specified in the prescription. In the alternative, the at least one other criteria may include at least one of a medical condition and habit of the medication user for which the prescription was rendered.

Here also there may be a plurality of different possible health safety functions that may be sponsored and the sponsor may sponsor only a subset of the possible functions and wherein the medication profiles include each include an indication of which functions may be sponsored.

One other apparatus is for providing container labels at least a sub-set of which include enhanced devices wherein each enhanced device may include data related to an order associated with the container, the apparatus comprising an enhanced label source providing labels including attached enhanced devices, a non-enhanced label source, a processor equipped to control the sources, the processor determining when an enhanced label should be used to identify the prescription and, when a non-enhanced label should be used, providing the non-enhanced label and when an enhanced label should be used providing the enhanced label and providing at least a subset of the data related to the order and a writer for receiving the enhanced labels and writing the data related to the order to the enhanced devices.

This apparatus may further including a printer linked to the processor for receiving both enhanced and non-enhanced labels, for each label, the processor providing at least a subset of the data related to the order to the printer for printing on a label.

Other apparatus are for use with a container, a data collector and an enhanced device, when the collector is juxtaposed in a specific orientation with respect to the enhanced device, the collector able to receive data stored on the enhanced device, the container and collector having first and second mechanical constraints that cooperate to position the collector adjacent an aligned section of the container, the apparatus for securing the enhanced device adjacent the aligned section, the apparatus comprising a device attacher positioned adjacent an attachment station, the attacher for attaching an enhanced device to a container section positioned within an attachment location within the station, an enhanced device source providing enhanced devices to the attacher and a container positioner for receiving the container and positioning the container at the attachment station such that the aligned section may be within the attachment location. Here, with the aligned section within the attachment location, the attacher attaches the enhanced device to the aligned section.

The positioner may include a third mechanical constraint receivable by the first mechanical constraint to control the position of the container. The container may be a vial and the first mechanical constraint may include at least one extension from the side of the container and the third mechanical constraint may include a keyed extension that abuts the at least one extension. The container may include a vial and a vial cap and wherein the collector may be formed within the cap.

Thus, another object is to provide a system wherein, when the container and a data collector include first and second mechanical constraints, respectively, that together align the collector and an enhanced device, the enhanced device positioning system operates to make sure that the enhanced device is in a specific location with respect to the first mechanical constraint so that the collector and the enhanced device properly align. This is accomplished by using a third mechanical constraint to position the container in a specific position with respect to an enhanced device attacher as explained in more detail below.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 15 is a user characteristics profile database useable in the process of FIG. 13.

FIG. 16 is a perspective view of a unique medication label including an enhanced device wherein the label is attached to a sheet for printing;

FIG. 17 is a perspective view of the enhanced label of FIG. 16, albeit with the label detached from a storage backing and of the label side opposite the side illustrated in FIG. 16;

FIG. 18 is a perspective view of the enhanced label of FIG. 17 attached to a vial.

DETAILED DESCRIPTION OF THE INVENTION

While the present invention may be used in many different industries where both human readable indicia and enhanced memory devices may be used together to provide information and to correlate that information, in order to simplify this explanation the present invention will be described in the context of medical prescription fulfillment where the need for dual communication modes is particularly relevant.

Figure 1:
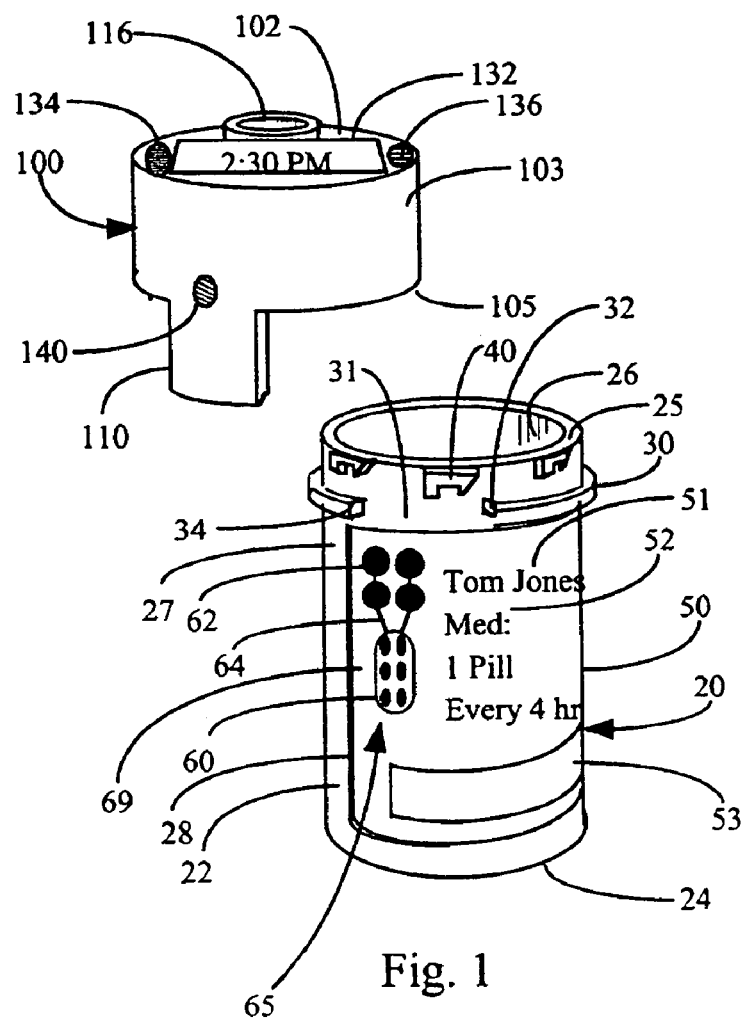
FIG. 1 is a perspective view of a container including an enhanced device useable with the present invention.

In addition, referring to FIG. 1, while the phrase "enhanced memory device" or derivatives thereof cover a wide variety of different memory devices (e.g., RFID tags, electronic memory, magnetic storage devices, multi-dimensional bar codes, multi-dimensional dot matrices and others) unless indicated otherwise the invention will only be described in the context of an electronic memory device 69 in order to simplify this explanation.

Moreover, referring still to FIG. 1, while the concept of an interactive device or data collecting device to facilitate use of data stored on enhanced devices includes many different devices (e.g., remotely used devices, stationary devices, etc.), the present invention will be described in the context of a an exemplary remote interacting device 100. For descriptions of additional interacting devices useful with the present invention see U.S. Pat. No. 5,852,590 that is titled "Interactive Label For Medication Containers And Dispensers" that issued on Dec. 22, 1998 and which is incorporated herein by reference. Generally interacting devices or data collectors may be either readers (i.e., capable of reading information from enhanced devices) or receivers (i.e., capable of receiving information from enhanced devices where the enhanced devices transmit information).

Furthermore, to distinguish between an interactive device (i.e., a code reader and processor for performing some function) user or customer and a customer or medication user that does not use an interactive device, interactive device users will be referred to as device users and all other customers will be referred to as non-device users.

In addition, while the present invention may be used to generate identifying configurations (i.e., labels) for any of several different container types (e.g., boxes, vials, IV bags, blister packs, etc.), the invention will be described in the context of a vial having a securable cap.

Referring to FIG. 1, an exemplary remote alert and recording system 10 includes a medication vial 20 and a reminder device in the form of an "intelligent" vial cap 100. Vial 20 includes a compartment 21 defined by a cylindrical wall 22, a closed bottom end 24 and an open top end 25. Medication 15 is inserted into and removed from the compartment 21 via open end 25. The cylinder has an inner surface 26 and an outer surface 27.

Vial 20 has several securement ratchets 40 for securing and sealing the cap 100 against the open end 26 of the vial. Ratchets 40 are evenly spaced around the open end 25, and protrude from the outer surface 27 of the vial 20. The ratchets are similar to those found on conventional childproof medication containers. Although the ratchets 40 are shown and described as being evenly spaced from each other as in a conventional vial, it should be understood that one or more of the ratchets could be offset.

Vial 20 also includes a second means for aligning cap 100 with vial 20. The second alignment means includes a guide ring 30 protruding from the outer surface 27 of the vial 20. The guide ring 30 is located at a substantially uniform, predetermined distance from the open end 25 of the vial. The guide ring surrounds most of wall 22. Ring 30 has an opening 31 defined by its two ends 32 and 34. Ends 32 and 34 are spaced apart a predetermined distance so that opening 31 has a predetermined size for accommodating a cap sensing tab 110 as discussed below. While the second alignment means is shown and described as being guide ring 30, it should be understood that other forms are contemplated. The vial 20 is made of a unitary piece of relatively rigid plastic similar to other conventional vial-type medication containers.

A label 50 is attached to outer surface 27 via any means (e.g., gluing) known in the art. Label 50 generally includes two sections, a textual portion or indicia section 52 for printing human readable indicia and an enhanced device section 65 for placement of an enhanced device 69. Section 52 is further divided into a specifying space 51 and an indicating space 53. Typical and relatively minimal prescription information is printed on space 51 including, for example; a medication user's name, the medication type, prescribed consumption schedule and perhaps some warnings regarding the medication to be stored in vial 20. An indicator indicating whether or not enhanced information is stored on device 69 is provided in space 53. For example, where enhanced information is provided on device 69, a human readable message such as "Enhanced device activated" may be printed in space 53. Where no information is provided on device 69, space 53 may be left blank or, in the alternative, a message such as "Enhanced device de-activated", may be provided in space 53.

While the invention is described in the context of container 100 and the exemplary labeling mechanism describe therein it should be appreciated that any manner of including human readable indicia on a container is contemplated such as printing the information on an external surface of the container, printing the information on a cap or undersurface of the container, where the container or a portion thereof is translucent, printing the information on the inside of the container and so on.

It is contemplated that much more information and, specifically, information that can be used by cap 100, is provided in a machine-readable format on device 69. For instance, a machine readable medication schedule may be provided on device 69 along with instructions (e.g., change the schedule if medication taken too early or too late) for what to do if a schedule is not followed. Many other useful information types are contemplated and have been described in the above referenced application that has been incorporated by reference.

Device 69 includes an electronic, machine readable and writable memory strip 60 that is similar to those used in commercially available smart cards, contacts 62 and wires 64 that link strip 60 to contacts 62. A protective coating (not illustrated) may be applied over the memory strip 60. Although the memory strip 60 is shown and described as being secured to a paper backing 51, it should be understood that the memory strip 60 could be affixed directly to the inner or outer surface 26 or 27 of the vial 20 or even embedded in the vial walls. While the memory device 60 is described and shown as having the shape of a strip, it should be understood that differently shaped memory devices could be used without departing from the invention.

Cap 100 includes a main body 101 with a top portion 102 and a cylindrical rim 103 having an inside surface (not numbered) and a lower edge 105. Cap 100 includes several hold down lugs (not illustrated) and a resilient disc much like those provided on conventional medication vial caps. The hold down lugs are located around the inside surface of rim 103 near its lower edge 105. The number of hold down lugs coincides with the number of ratchets 40, and the lugs are evenly spaced to align with ratchets 40. The resilient disc is attached to the inside surface of cap 100.

Cap 100 includes a sensing device, data collector or sensing tab 110 for sensing contacts 62. The tab 110 forms a first mechanical constraint that cooperates with a second mechanical constraint on the vial to align the tab with contacts 62. The sensing tab 110 projects down from edge 105 of rim 103 of cap 100. Tab 110 has an inside surface with sensors (not illustrated) positioned to align with contacts 62 when cap 100 is in a secured position on the open end 25 of vial 20. The sensors electrically engage contacts 62 and predetermined information stored on memory strip 60 is electronically received (i.e., transmitted to or otherwise communicated or read by) a processor within cap 100.

Although not illustrated, cap 100 includes a processor, a memory, a power source (e.g., a battery), a timing device and the contacts mentioned above (none of which are illustrated). In addition, cap 100 includes a relatively small display 132 (e.g., and LCD display), audible and/or visual alarms 134, 136, an activation button 16 and an infrared transceiver 140. Each of components 132, 134, 136, 16 and 140 along with the memory and the cap contacts are linked to and controlled by the processor. Alarms 134, 136 and display 132 may be used to indicate a variety of warnings to a patient, such as when it is time to take a dose of medication. Button 16 can be used to communicate with the processor. For instance, to turn off an alarm button 16 may be depressed or to indicate that medication has been consumed button 16 may be pressed in a specific sequence (e.g., three rapid depressions). The timing device informs the processor when a predetermined time to take medication occurs. The processor then informs a medication user that it is time to take a dose of medication via the display 132 or an alarm 134, 136. For a more detailed description of cap 100 refer to the application referenced and incorporated by reference above.

The ratchets 40 interact with the hold down lugs to form a relatively tight, child resistant or childproof seal between the cap 100 and the vial 20. This is accomplished by placing the cap 100 over the open end 25 of the vial 20 so the lugs are aligned directly between the ratchets 40. The cap seals the open end 25 of the vial 20 when in this removably aligned position, but the cap is not secured to the vial. The cap 100 is then depressed and rotated clockwise so that each lugs slide into secure positions relative to the ratchets 40. The hold down lugs and ratchets 40 prevent the simple counterclockwise rotation of the cap, and thus its removal.

When cap 100 is secured to vial 20, tab 110 extends through the opening 31 in the guide ring 30 (i.e., ring 30 is the second mechanical constraint). The opening 31 is sized so that the cap 100 can only be attached to the vial 20 in the one position that aligns the sensors of tab 110 with contacts 62. Specifically, cap 100 can only be placed on the open end 25 of the vial 20 with the sensing tab 110 abutting or nearly abutting the right end 32 of the guide ring 30. Cap 100 is then rotated in a clockwise direction until the sensing tab 110 abuts or nearly abuts left end 34 of ring 30 and the hold down lugs and ratchets 40 have locked together to secure cap 100 to vial 20.

Referring still to FIG. 1, vial 20 further includes a first means for aligning the interactive label 50 with a predetermined location of wall 22. This alignment means is accomplished by forming a recess 28 in the outer surface 27 of the wall 22. An inwardly projecting ridge 29 that extends around the perimeter of the recess defines the recess 28. While this first alignment means is shown as recess 28, it should be understood that it could take on a variety of forms. For example, an outwardly projecting ridge (not shown) protruding from wall 22, or a raised substantially flat platform (not shown) protruding from the wall could be used. It should also be understood that the label 50 could be located on the inside surface 26 of the vial 20 without departing from the broad aspects of the invention. Label 50 is affixed in recess 28 so that the left edge of the label abuts and is aligned with the ridge forming the left side of recess 28. The upper edge of the label 50 abuts the ridge forming the upper side of the recess 28. This alignment positions the label 50 in a desired location on the wall 22 of the vial 20 so that space 65 is in a location that, when cap 100 is secured to vial 20, is adjacent the sensor on the inside of tab 110. To this end there is an important mechanically dimensioned relationship between the guide ring 30, the tab 110, the label 50 including space 65 and the recess 28 that ensures that the cap sensor and space 65 align and that spaces 52 and 53 are visible to a vial user so that indicia in spaces 52 and 53 can be read by the user.

Thus, label 50 includes two ways of "storing" information including human readable and visible indicia printed on space 52 and machine-readable data on memory device 69.

The embodiments that follow describe several methods and apparatuses for specifying container-indicating configurations and to provide indicators (i.e., enhanced and printed)

on the outside of containers. Nevertheless, it should be understood that the invention contemplates many other versions of the invention.

FIRST EMBODIMENT

Figure 2:
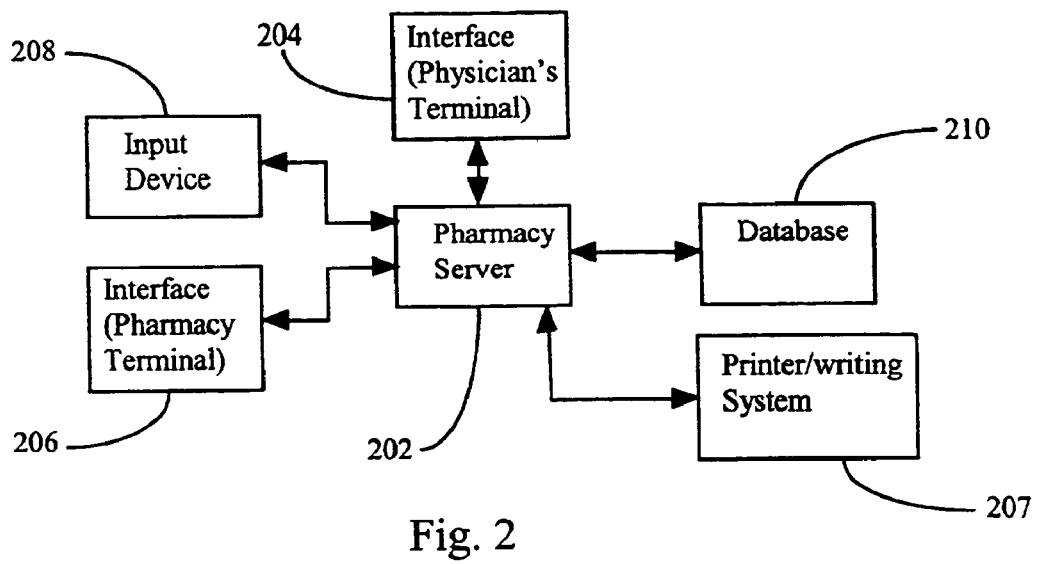
FIG. 2 is a schematic diagram of a configuring system.

Referring now to FIG. 2, a first embodiment of the present invention is described in the context of an exemplary computer system 200 including a server 202, interfaces 204 and 206, an input device 208, a printing system 207 and a database 210 that are linked together via a computer network such as a wide area network or the Internet. It should be appreciated that the illustrated system is relatively simple and that an actual system would likely include many more components. The simple system is employed to describe the present invention in the interest of brevity.

Server 202 is linked to each of interfaces 204 and 206 and input device 208 for receiving information therefrom and providing information back to system users. In addition, server 202 is linked to database 210 for reading information from and writing information to the database 210. Server 202 runs a computer program to perform various pharmacy functions including receiving prescriptions, instructing pharmacists on how to fill prescriptions, providing instructions on consuming medications, organizing and stocking inventory and so on.

Referring still to FIG. 2, interface 204 is a terminal that resides in a physician's office and which is used to communicate with server 202. To this end, while terminal 204 may be a dedicated terminal for pharmacy communication only, it is contemplated that interface 204 may be a standard personal computer or network computer used for any office tasks that is also useable, via a standard browser package, to communicate prescriptions to the pharmacy server 202.

Interface 206 is similar to interface 204 except that interface 206 resides at a pharmacy instead of at a physician's office. To this end, in one embodiment interface 206 is personal computer or simple terminal for communicating prescriptions to server 202 and for receiving useful information back from server 202.

Input device 208 is a simple device for indicating whether or not a pharmacy customer uses or has access to an "interacting device" for interacting with enhanced memory devices and, perhaps, also to provide other information required to support functions for the interactive device user. In the present example input device 208 is used to indicate whether or not a customer uses an electronic device reader and processor (i.e., whether or not the user is a device user) at home or at remote locations to facilitate automated health safety functions. In the present example, device 208 is used to indicate whether or not a customer uses device 100 in FIG. 1.

It should be appreciated that device 208 may not be a separate device but instead may be part of either of interfaces 204 or 206 or some other input system such as a system at a retail store where devices 100 may be sold. In this explanation device 208 is shown as a dedicated device to clearly indicate the import of device 208's function and to stress the fact that device 208 may be separate from the interfaces 204 and 206. In any event, after a pharmacy customer obtains an interactive device 100 for home or remote use (i.e., becomes a device user), input device 208 is used to indicate that the customer is a device user. User indications are provided to server 202 that in turn stores such indications, correlated with user identification information (i.e., the user's name or a user identification number) in database 210 for future use.

In addition, device 208 may also be equipped to receive other specifying information for specifying which of several different functions the user's device 100 supports and which functions the user or the user's physician wants to take advantage of. For example, some devices 100 may only be capable of indicating medication consumption times while others may be capable of both indicating consumption times and storing consumption times in the device memory for subsequent downloading and permanent storage.

Another device 100 may be equipped to support a physician notification function when mis-medication occurs. For example, upon indicating a consumption time and failing to sense that cap 100 has been removed, the cap 100 processor may assume that medication has not been consumed and may indicate mis-medication via infra-red transceiver 140 to some other device (not illustrated) such as a stand alone medication base station that is linked via a computer network to a physician's terminal (e.g., 204 in FIG. 2). In this case, when mis-medication occurs, the network linked base station may send an e-mail to the physician warning that mis-medication occurred. Still other devices 100 may support any of several other functions and other device embodiments may support even more functions. For a discussion of other devices and supportable functions see the above referenced patent that has been included herein by reference.

In the alternative, some systems may support only a small number of functions and each system user may be required to use all of the supported functions and, in this case, the function support specifying process may be skipped.

Moreover, device 208 may also be equipped to provide additional information required to support certain functions. For example, in the case of a device 100 that cooperates with a medication base station to e-mail mis-medication warnings to physician's, in addition to sending a mis-medication e-mail to a prescribing physician, it may also be necessary or at least advantageous to send such a warning to a primary physician. This feature may be particularly important as patients often seek service from several physicians due to specialties and scheduling considerations. In this case the primary physician's e-mail address may be provided once via device 208 and used thereafter to support the mis-medication warning function. Other types of supporting information are contemplated.

Furthermore, device 208 may also be used to indicate additional information that is required for specific medications that might be prescribed. For example, a pharmacist may require a specific warning to be provided to a device user each time the user is reminded to consume a medication. For example, some medications may have to be taken on a full stomach. In this case, each time a user is reminded to consume, screen 132 may be used to remind the user to take after a meal. This type of warning may be specified via device 208.

Thus, device 208 may be used to specify four different information types including (1) that a medication consumer uses an interactive device (e.g., 100), (2) which of several functions the system user wants to take advantage of, (3) additional information required to support the selected functions and (4) additional information required for each specific medication that is prescribed. All of the information entered via device 208 is correlated with a customer or user identifier and is stored in database 210.

Although not described in detail here it is contemplated that input device 208 may include software that walks a pharmacist or the like through a series of questions in order to help the pharmacist configure a profile for each customer that uses an interactive device (e.g., 100 in FIG. 1).

Figure 3:
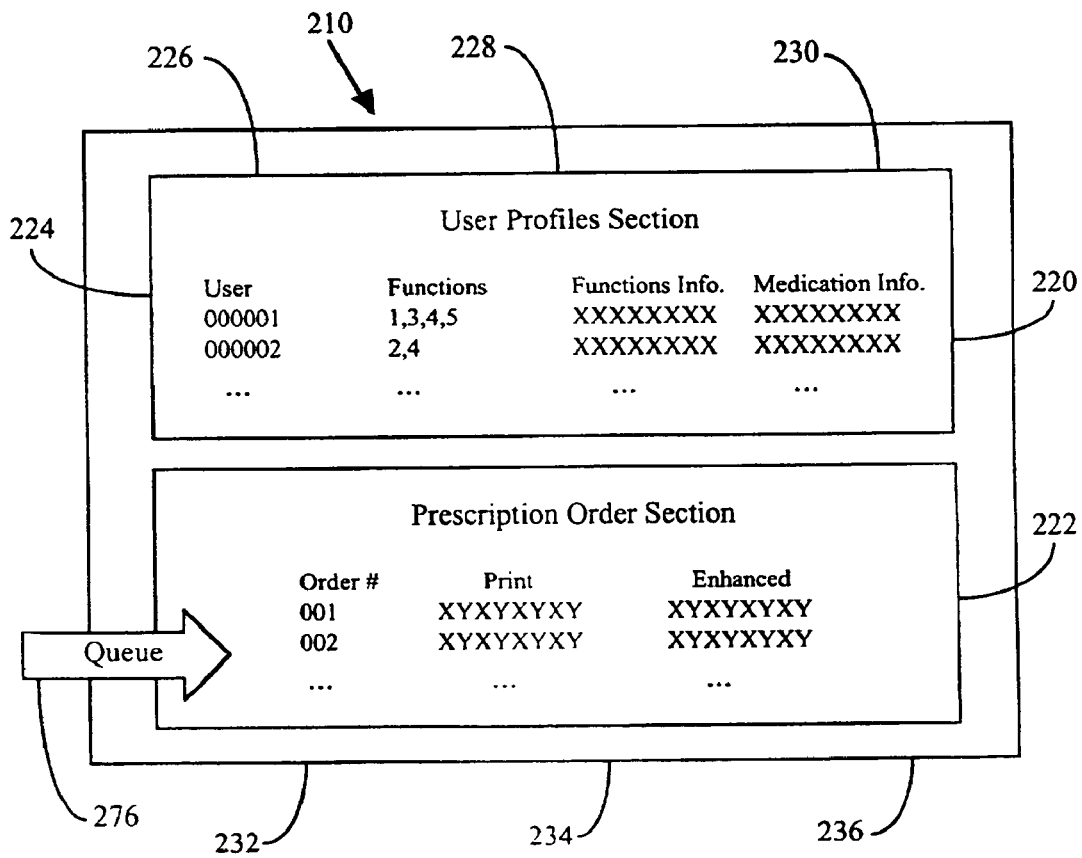
FIG. 3 is a schematic diagram of the database of FIG. 2.

Referring now to FIG. 3, database 210 includes two separate sections including a user profile section 220 and a prescription order list 222. All of the information described above that is input via input device 208 is stored, in a correlated format, in profile section 220 with user information. To this end section 220 includes four columns, a user column 224, a function column 226, a function information column 228 and a medication information column 230. As illustrated, each pharmacy user is provided with a unique user # in column 224. In column 226 functions corresponding to each user in column 224 are identified. In the illustration the functions are identified in a simplified form via numerals 1, 2, etc. to simplify this explanation. Nevertheless, it should be appreciated that each of the function numbers corresponds to any of several different health safety functions such as generating a consumption time alert, storing consumption time information, identifying contraindicating information and so on. In column 228 the information required for each of the functions in column 226 is specified and in column 230 the information required for specific medications is specified.

Order section 222 includes three columns including an order column 232, a "print" column 234 and an "enhanced" column 236. In order column 232 each physician prescribed order for the particular pharmacy is listed and identified by a unique order number (e.g., 001, 002, etc.). In print column 234 a list of information to be printed on indicia section 52 of a label 50 (see also FIG. 1) is provided. In enhanced column 236 a list of information to be written to device 69 is provided.

Figure 4:
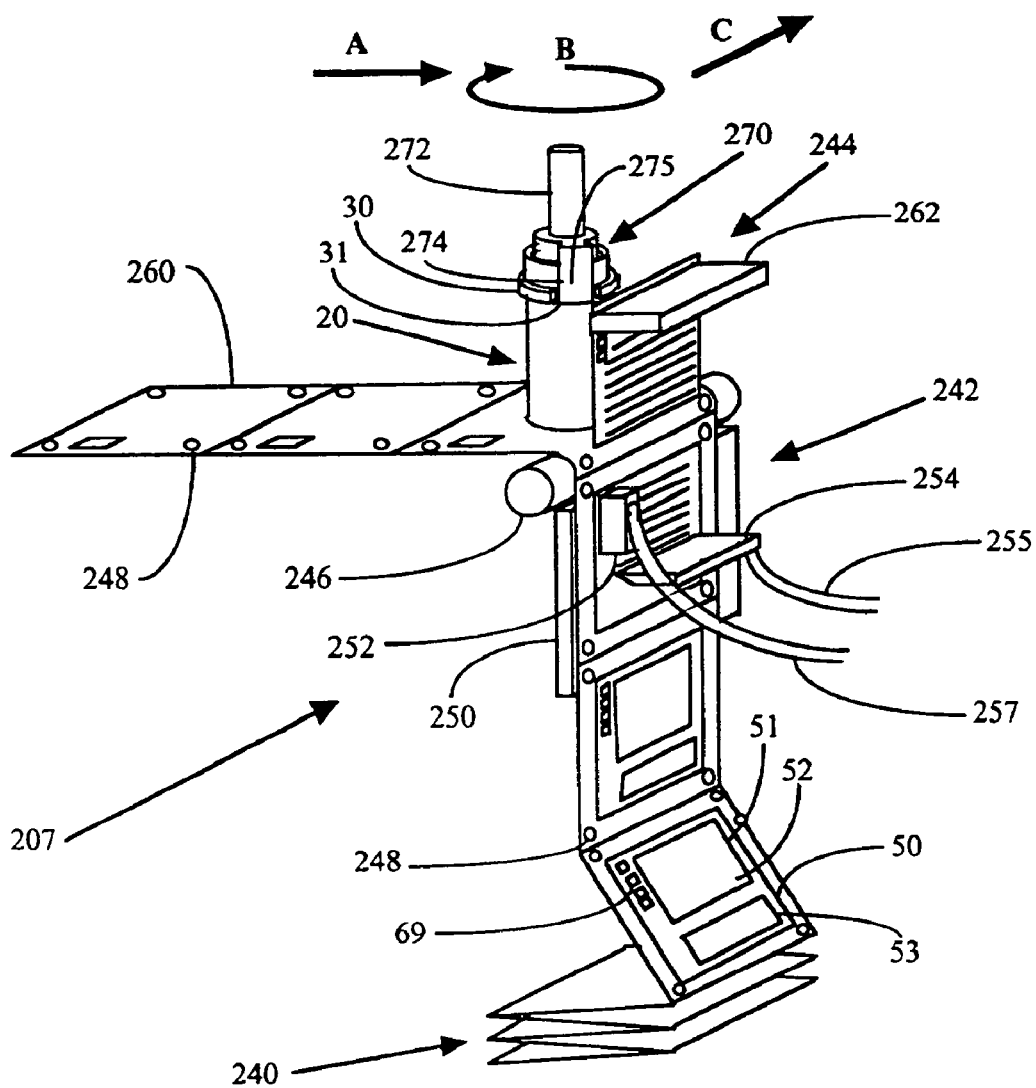
FIG. 4 is a perspective view of part of one printing/writing system of FIG. 2.

Referring now to FIG. 4, printing system 207 is used to perform "specifying" processes including printing human readable indicia for inclusion on containers and writing machine readable information to enhanced devices. System 207 includes, label source 240, a printing/writing station 242 and a labeling or attachment station 244. Source 240 includes a plurality of labels (e.g., 50) mounted to a paper backing 260 that is folded, accordion style, below specifying station 242. Each label 50 includes an indicia section 52 and an electronic memory device 69 as described above. The paper backing 260 includes indexing holes collectively referred to by numeral 248 that are used to draw the labels into specifying and labeling positions as described in more detail below.

Printing/writing station 242 includes a roller 246, a specifying plate 250, an electronic data writer 252 and an indicia provider or printer head 254. Plate 250 includes a support surface (not separately numbered) slightly larger than the label size for supporting labels during printing and writing processes. In the illustrated embodiment plate 250 is vertically arranged above source 240. Roller 246 is positioned above plate 250 and may including indexing pins (not illustrated) for engaging holes 248 and driving the labels throughout the labeling process.

Writer 252 is positioned adjacent plate 250 in a position that is proximate each enhanced device 69 when the label including the device is positioned adjacent plate 250. Thus, writer 252 is positioned so that data can be written to a device 69. Similarly, printer head 254 is positioned adjacent plate 250 such that the head is proximate an indicia section 52 of each label when the label is adjacent and supported by plate 250. Data cables 255 and 257 link each of the head 254 and writer 252 to processor 202 for data and information control, respectively.

Although not illustrated printing system 207 would also include additional rollers (e.g., 246) for guiding the labels 50 and paper backing 260 during a labeling process. When a label is moved to a position adjacent plate 250, if the person for which medication has been prescribed uses an interactive device (i.e., 100 in FIG. 1), information is written to device 69 and other information is printed on indicia section 52. In the alternative, if the person for which the prescription was provided does not use an interactive device, only printed information is provided on section 52 and no information is provided on device 69.

Referring still to FIG. 4, after printing and writing information to a label 50, the label is moved upward and another label is pulled into a position adjacent plate 250. As a label 50 is moved upward beyond plate 250, the paper backing is pulled horizontally about roller 246 such that the label becomes unstuck and continues to move vertically.

Labeling or attachment station 244 includes a vial positioner or support 270 and suction head or device attacher 262. Head/attacher 262 aids in the un-sticking process. Head 262 is positioned above roller 246 and abuts labels 50 as they become detached from backing 260. To this end, head 262 forms a vacuum on the outer surface of each label 50 and thereby pulls the labels from the backing 260. Once pulled from the backing the label is held in a position such that the enhanced device 69 is adjacent an attachment location (see location of vial in FIG. 4). Then, when a vial is positioned adjacent the attacher 244, the attacher advances and attaches the label to the vial.

Positioner or support 270 includes a shaft 272 and a third mechanical extension or keyed receptor 274 that extends laterally from an external surface of the vial. Receptor 274 is constructed to secure to the top surface of a vial (e.g., see 20 in FIG. 1) and is integrally linked to shaft 272. In addition to supporting vial 20, receptor 274 is constructed such that the specific rotational position of vial 20 can be controlled. In this regard, receptor 274 includes a keyed extension 275 that is sized so as to be received within the opening 31 within rim 30. Thus, by rotating receptor 274 so that key 275 is in a known rotational position, the vial position is also known.

Shaft 272 is rotatable about a central axis in the direction indicated by arrow B and is also moveable from a vial source along the direction indicated by arrow A and to a vial destination location along the direction indicated by arrow C. Although only one shaft 272 and receptor 274 are illustrated it is contemplated that system 207 would likely include a plurality of shafts and receptors to move vials from the source to the labeling station and then off to the destination location to be filled with medications.

Shaft 272 and receptor 274 are positioned relative to a label (e.g., 50) to be attached such that, when the label is attached, device 69 will be positioned with respect to the opening 31 so that the contacts on cap 100 will be aligned with device 69 for reading purposes. With a vial 20 positioned adjacent a label 50 that is supported by head 262, label 50 is moved toward vial 20 until one end of the sticky side of the label 50 contacts the external surface of the vial 20. Then, shaft 272 is rotated thereby causing the linked vial to rotate such that the label is applied to the external vial surface. Next, shaft 272 is moved in direction C and another vial is brought into the labeling station 244 while another sticker is advanced and detached from backing 260. Thus, according to one method the first and third mechanical constraints are juxtaposed such that an attachment location for the enhanced device 69 places the device in a position for reading by a cap as illustrated in FIG. 1.

In operation, referring to FIGS. 1 through 4, when a medication user purchases or otherwise gains access to an interactive device 100, the user or some other system user such as a physician or a pharmacist uses device 208 to indicate that the user will be using an interactive device 100. In addition, the person entering the information via device 208 also indicates which of several different functions the user wishes to use and provides any other additional information required to support the selected functions. The entered information is arranged via server 202 and stored in user profile section 220 of database 210.

With the user profile specified and stored, upon a physician prescribing a particular medication via interface 204 (or, in the alternative, on paper, the prescription then entered via pharmacist's terminal 206), server 202 receives the prescription information specifying the person for which the medication was prescribed, the type of medication, the dose prescribed, and any other relevant information. When the prescription information is received, server 202 attempts to correlate the patient information with one of the user identifiers in column 224. Where the patient information corresponds to one of the users specified in column 224, the user is an interactive device user and is recognized as such. In the alternative, server 202 recognizes that the user is not an interactive device user. In either case server 202 forms an order for the prescription and stores the order in the order list in section 222.

To this end, where the user is an interactive device user, the formed order includes information in the enhanced column 236 that is to be written to an enhanced data storage device (e.g., 69 in FIG. 1). Where the user is not an interactive device user the formed order does not include information in the enhanced column 236 or may include a null character string (e.g., 0000) indicating a user that does not use an interactive device. As additional orders come into the pharmacy, the orders are added onto the order list in section 222.

When there is at least one order in section 222, server 202 selects the order and for providing a vial for storing the medication corresponding to the specific order. Where there are several orders in section 222, server 202 selects the orders sequentially on a first in first out basis to provide vials for storing the corresponding medications. To track the orders for which vials have been provided server 202 maintains a queue pointer 276 in database 210 that points to an order corresponding to a vial for which information is currently being printed and/or written to the indicia section 52 and device 69, respectively.

With the orders stored and queue 276 specified, server 202 selects the order corresponding to queue 276 for printing and writing. If the order corresponding to the queue includes information in enhanced column 236, server 202 writes the enhanced information to device 69 via writer 252 while printer head 254 prints information on indicia section 52. If the order corresponding to the queue does not include information in enhanced column 236 then server 202 only causes head 254 to print information and writer 252 is disabled.

Where information is written to device 69, in addition to printing the specified information to indicia space 51, server 202 may also cause head 254 to print a message (e.g., "Enhanced device is activated") to space 53 (see FIG. 1) indicating that device 69 includes information to be used by an interacting device. Moreover, head 254 may also print a message in space 53 indicating inactivation of device 69 if no information is provided to device 69.

After information is printed and perhaps also written to section 52 and device 69, respectively, roller 246 and other rollers (not illustrated) move backing 260 so that the newly specified label is moved upward. Suction head 262 forms a vacuum on the exterior surface of the label 50 thereby causing the label to un-stick from backing 260. Label 50 is then secured to the outside or exterior surface of a vial 20 in the manner described above. After the specified label 50 is attached to the vial 20, the vial is moved to the destination location along direction C. Although not illustrated it is contemplated that the destination location is simply an output area that provides the labeled vials to a pharmacist. The pharmacist can then read the prescription form indicia section 52 and fill the vial in a manner consistent with the indicia.

While not illustrated it is also contemplated that the system may automatically fill the vials with medications either before or after the labeling and writing processes. In addition, in another embodiment the system may allow a pharmacist to manually fill the vials prior to labeling and writing. Moreover, the system could be configured to automatically place a cap on vials after the vials have been filled with medication.

In a version of the embodiment described above, writer 252 is replaced with a writer/reader 252 which, as the name implies, can read and write information from and to device 69. In this case, after enhanced information is written to device 69, writer/reader 252 can read the information stored on device 69 and provide that information back to server 202. Server 202 can then compare the information that was to be written to device 69 with the information actually written to device 69 to make sure that the two information sets are identical. If the information is identical system 207 may advance the specified vial to the destination location. If the two information sets are not identical, server 202 may ether attempt to rewrite the information to device 69 and then reconfirm that the written information is correct or, in the alternative, may scrap the label and attempt to print and write the information and data to a new label 50 advanced from source 240.

Thus, it should be appreciated that this first embodiment of the invention overcomes many of the problems described above. For instance, this system automatically ensures that the information written to an enhanced device (i.e., an electronic memory) is correlated with the information printed on indicia section 52. This is accomplished by printing and writing simultaneously from the same order. In addition, where a reader/writer 252 are provided as part of printing system 207, server 202 can verify that written information matches the information that was to be written to a particular label and therefore that the information on the enhanced device 69 is correct. Moreover, by providing a human readable message in indicator space 53 (see FIG. 1), a pharmacist and a medication user can each independently ensure that information has been provided to device 69 when such information should be provided. Furthermore, the system can automatically place a label on a vial in the precise location required to ensure that the sensor on the inside of tab 110 is aligned with the enhanced device 69. In addition, by writing consumption data to device 69 the vial is enabled to help facilitate prescribed medication regimens and thus avoid mis-medication.

While database sections 220 and 222 are identified as being part of single database 210, it is contemplated that each section may comprise a separate database accessible to server 202 is some fashion. In fact, it has been recognized that while order section 222 is most likely pharmacy dependent, section 220 will often be relevant to more than a single pharmacy and therefore data is section 220 should likely be stored in a more globally accessible and searchable location than pharmacy server 202. For instance, often medication users will fill different prescriptions at several different pharmacies depending on location and convenience and therefore locating user profile information on a single pharmacy server 202 may render such information difficult if not impossible to access. While section 220 could be duplicated on several different databases, once for each pharmacy, such duplicity would be difficult to maintain and update. For instance, if an interactive device user currently uses functions 1, 2 and 3 (see FIG. 3, col. 226) and wishes to ad an additional function 13, the updated function set would have to be communicated to every pharmacy server that stores a profile for the particular user. Clearly such maintenance processes would be extremely burdensome.

One contemplated location for section 220 data is a clearinghouse server accessible by member pharmacies where any pharmacy that receives a prescription can access a clearinghouse database to determine if the prescribee is an interactive device user. In this case it is contemplated that when a pharmacist enters a prescribee's name or an identification number via terminal 26, the identifier is sent to the clearing house server which then searches the clearing house database to determine if the user is an interactive device user. Where the user is a device user the clearinghouse server then provides the information for the user back to the pharmacy server so that an order can be formed and placed in the section 222 queue 276.

Another contemplated location for section 220 is a smart card or some other personal medication user device such as a personal digital assistant (PDA). In this case, upon a request to fill a prescription, the user presents his smart card or the like to a pharmacist and the user profile is downloaded therefrom into the pharmacy server 202 so that a proper order can be formed.

In either of these two cases the access and maintenance problems associated with storing user profiles on a single pharmacy server are essentially eliminated.

SECOND EMBODIMENT

Figure 5:
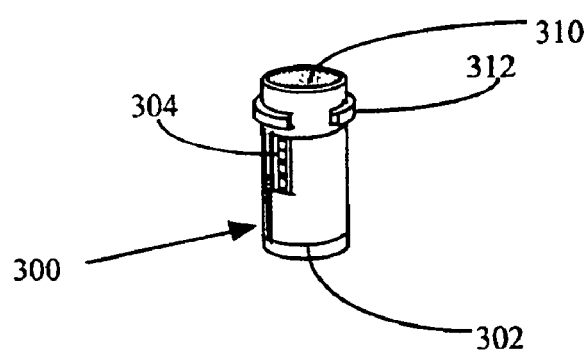
FIG. 5 is a perspective view of a container assembly similar to the assembly of FIG. 1.

Referring now to FIG. 5, a vial 300 forming a compartment 310 and corresponding label 302 and enhanced device 304 similar to vial 20, label 50 and enhanced device 69 in FIG. 1 are illustrated. In this embodiment, however instead of proving enhanced or electronic memory device 304 on label 302, device 304 is integrally secured to an external surface of vial 300 and is separate from label 302. Vial 300, like vial 20, includes a guide ring 312 and, although not illustrated, would include ratchets (e.g., 40 in FIG. 1) for guiding an intelligent cap into alignment with device 304 for reading purposes. Vial 300 is meant to be used with a cap like cap 100 in FIG. 1 and therefore cap 100 will not be explained again here in detail.

Figure 6:
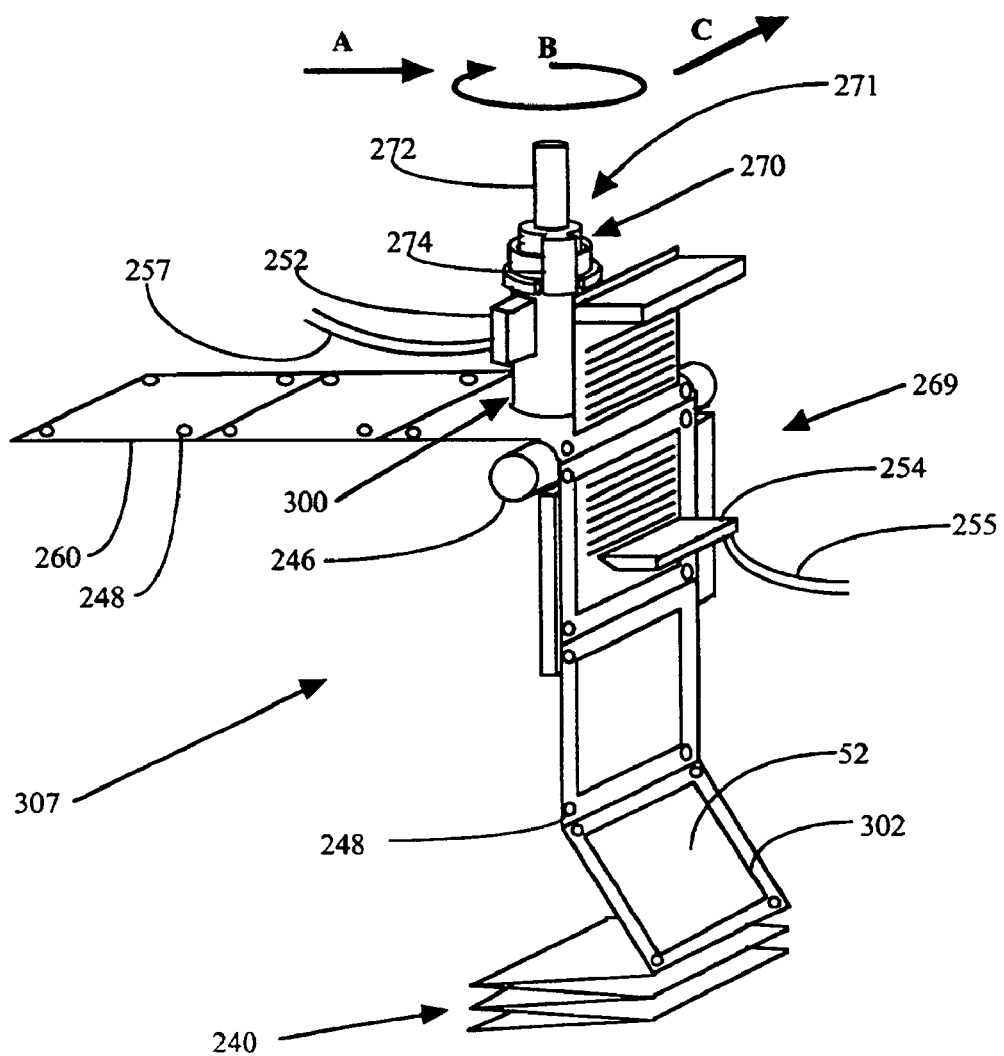
FIG. 6 is similar to FIG. 4, albeit illustrating one other embodiment of the printing/writing system of FIG. 2.

Referring also to FIG. 6, a printing system 307 similar to system 207 of FIG. 4 is illustrated. Many of the components of system 307 are identical to the components of system 207 and therefore are identified by similar numbers and will not be explained again here in detail. In this case, the main difference is twofold. First, the printing and writing steps are sequential instead of simultaneous to accommodate hardware constraints. To this end a first station is a printing station 269 while the second station is a label/write station 271. At print station 269, as the name implies, human readable indicia are printed on a space 52. At the label/write station 271, a printed label is attached to the vial 300 and data is written to device 304.

Second, the server 202 (see FIG. 2) must be programmed to sequence the writing and printing steps so that the writing steps follow their associated printing steps by a specific number of printing cycles to ensure that the information written to a device 304 corresponds to the printed information on indicia space 52. In the illustrated embodiment the information is printed to section 52 one cycle prior to writer 252 writing the information to device 304 and therefore the sequence is to (1) print information during a first cycle and (2) write corresponding information during a next sequential cycle. In this embodiment, like the first embodiment, it is contemplated that server 202 would disable writer 252 whenever data is not to be written to a device 304 (i.e., when a medication user does not use an interactive reader device).

THIRD EMBODIMENT

Referring again to FIGS. 2 and 6, according to a third embodiment of the invention, server 202 and interface 206 can cooperate to identify interactive device users and communicate to a pharmacist which type of vial, enhanced and including a device 304 or non-enhanced and thus not including a device 304, should be used to fill a prescription. To this end it is contemplated that receptor 274 and shaft 272 may be equipped for manual loading of vials so that a pharmacist can provide either of an enhanced vial (i.e., a vial including a device 304) or a standard vial (i.e., a vial that does not include a device 69).

In this embodiment, after server 202 causes information corresponding to an order to be printed on a label 50 and advances the label up to a position adjacent the label/write station 271, server 202 communicates with the pharmacist via interface 206 indicating which vial type to use for storing a specific prescription. To this end, server 202 simply determines if any enhanced information corresponding to the specific order is stored in the prescription order section 222 (see FIG. 3). If enhanced information corresponds to the order, server 202 indicates that an enhanced vial is required and instructs the pharmacist to load an enhanced vial onto the end of receptor 274. If enhanced information does not correspond to the order, server 202 indicates that a standard vial should be loaded onto the end of receptor 274.

The system may include a sensor at the end of receptor 274 to sense when a vial has been mounted to the end thereof. In the alternative, interface 206 may be equipped to receive an indication from the pharmacist that a vial has been loaded. For instance, a "Vial Loaded" icon may be selectable on an interface screen to indicate that loading has been completed.

After the required type of vial has been attached to the end of receptor 274, server 202 controls shaft to move the receptor and vial into a position at write/label station 271. With a vial placed at station 271, in some embodiments it may be advantageous to include some type of sensor at station 271 to ensure that the correct vial type is present. While any sensor type known in the art could be used for this purpose, one simple way to determine vial type is to attempt to write to a smart device (i.e., 69) using writer 300 and monitoring to determine if data was written. In this embodiment writer 300 would also include some means for reading data written to a device 69 to confirm presence or absence of a device 69. Here, either "test" information can be written or, in the case where an enhanced vial is to be used to store a medication, the actual data to be stored on a device 69 may be written. After data is written head 300 attempts to read the data. Where the written data can be read a device 69 is obviously present. Where data cannot be read it is assumed that no device 69 is present. Indicators can be included to alert a pharmacist when an incorrect vial type has been provided on receptor 274 so that correction can be made.

Once the correct vial type has been confirmed, server 202 causes the label 302 to be attached to the vial.

FOURTH EMBODIMENT

According to yet a fourth embodiment of the invention, referring again to FIG. 1, server 202 may simply indicate to a pharmacist, via interface 206, the vial type to be used to store a specific medication. For instance, referring again to FIG. 3, where a first order 001 includes enhanced information in column 236 server 202 indicates that an enhanced vial 304 is required. Similarly, where a second order 002 does not include enhanced information in column 236, server 202 indicates that a standard vial is required. Thereafter the pharmacist retrieves a vial of the indicated type for storing the medication. A standard label printer may then be used to print a label for the vial, the pharmacist retrieving the printed label and manually attaching the label to the vial. After the information is printed on the label, in the case of an enhanced vial, the information corresponding to the order is written to the device (e.g., 304).

In this case it has been recognized that there is a "manual disconnect" within the printing and writing process that could lead to a mismatch between the printed information and the written information. For example, a label printer in a busy pharmacist may pump out labels one after another to be attached to vials. In this case, if there is a label bottleneck, after a label is attached to a vial, if the vials are filled out of sequence, determining which enhanced data corresponds to which printed label and corresponding vial would be difficult.

To eliminate this correlation problem, the invention includes a method for correlation including, for orders that require enhanced vials, providing on the printed label a machine readable descriptor that identifies the order (e.g., see FIG. 3) corresponding to the printed label, after a label has been printed and attached to an enhanced device, reading the descriptor to identify the order, retrieving the enhanced data from the order and writing the enhanced data to the enhanced device. In this manner the need for an enhanced vial is indicated by the presence of a descriptor printed in space 408. In addition this method essentially assures complete correlation of printed and written data.

Figure 7:
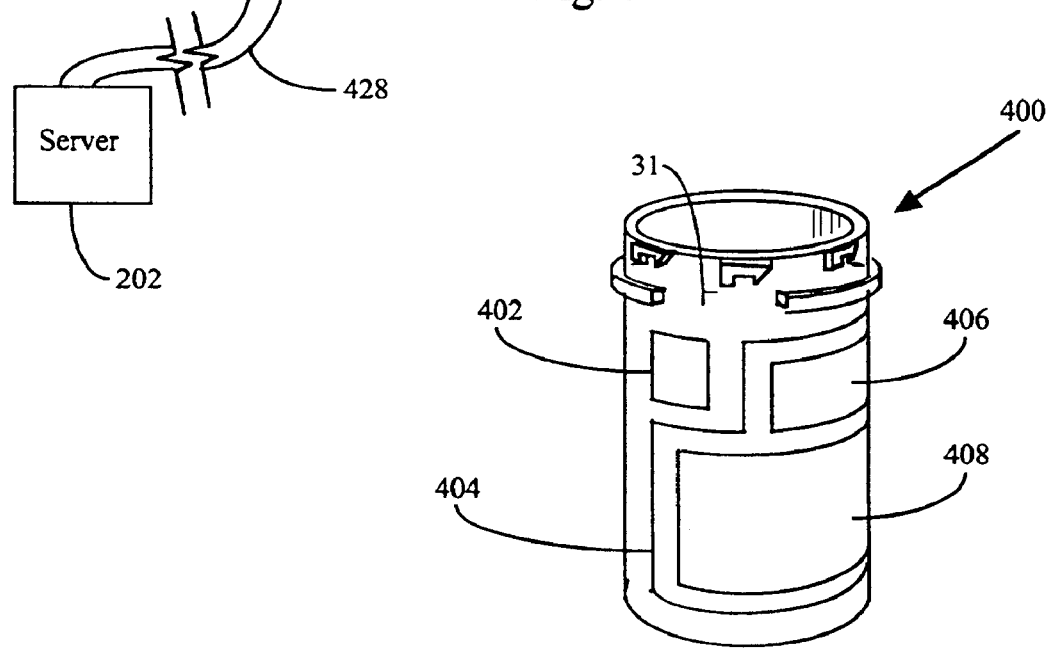
FIG. 7 is a perspective view of yet a third container.

Referring now to FIG. 7, therein is illustrated an enhanced vial 400 which is similar to the vial 300 in FIG. 5 in that vial 400 includes an enhanced device 402 mounted relative to a rim opening 31 and a label 404. The difference between vials 300 and 400 is that label 404 includes first and second spaces wherein the first space 406 is for printing human readable indicia and the second space 408 is for printing machine-readable. For instance, the human readable indicia may identify a medication user, a prescribing physician, a consumption regimen, etc. The machine readable indicia may include a bar code or some other machine recognizable code that indicates which of several different prescription orders in prescription order section 222 (see FIG. 3) the printed material corresponds to.

It should be appreciated that the machine-readable indicia may also be human readable in the case where the system includes an optical text reader or the like. In this regard the human and machine-readable indicia may be one in the same in some embodiments.

Figure 8:
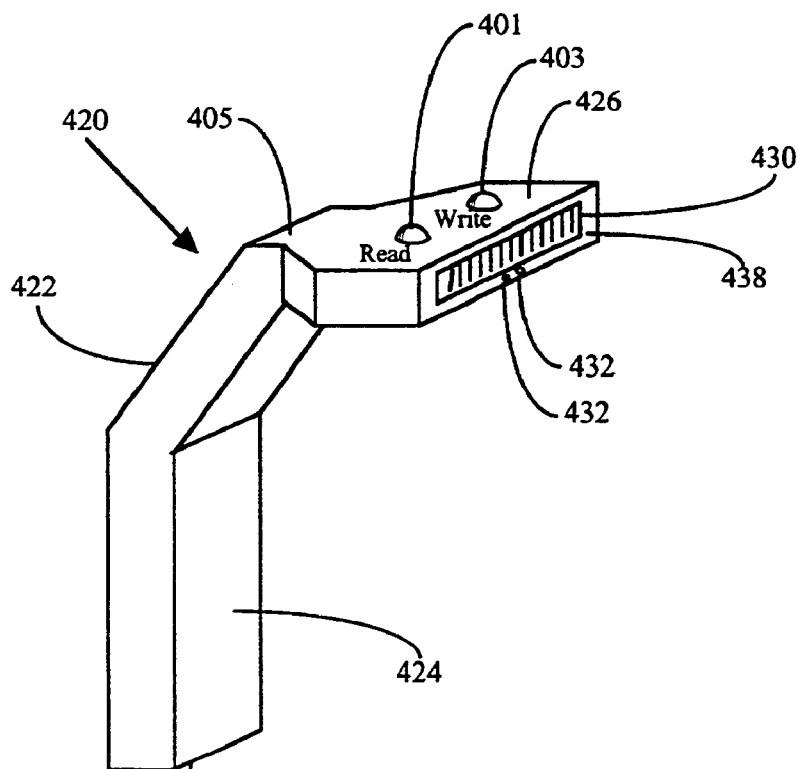
FIG. 8 is a perspective view of a hand held data reading and writing device.

Referring also to FIG. 8 a handheld reading and writing device (HHD) 420 is illustrated. HHD 420 includes a plastic housing 422 shaped to be comfortably received in a HHD user's hand and, to that end, includes a handle member 424 and a head member 426. Head member 426 includes a reader device 430 and a writer device 432 that are each mounted in a front surface 438. Reader device 430 is configured to accommodate the machine-readable information printed in space 408 (see FIG. 7). For example, where the machine-readable code is a simple bar code, device 430 is a bar code reader.

Writer device 432 is configured such that device 432 can write information to enhanced device 402. For example, where device 402 is an electronic memory having electronic contacts for reading and writing purposes, device 432 also includes electronic contacts arranged to mate with the contacts on enhanced device 402. In the alternative, where enhanced device is an RFID tag, writer device 432 may be an RF transmitter for transmitting information to device 402 when device 402 is proximate surface 438.

A cable 428 extends from a lower end of HHD 420 and is linked to server 202 as illustrated. Cable 428 provides information read from space 408 to server 202 and provides information from server 202 back to HHD 420 that is to be written to enhanced device 402.

In addition to the components described above, HHD 420 also includes read and write indicator lights 401 and 403 (e.g., LEDs), respectively, positioned on a top surface 405 of housing 422. Light 401 is activated when reader device 430 has completed reading data while light 403 is activated when writer device 432 has completed writing data to an enhanced device 402.

In operation, referring to FIGS. 2, 3, 7 and 8, when an order requiring an enhanced vial 400 comes up in the queue 276, server 202 causes a printer system to print a label corresponding to the order that includes both the desired human readable indicia in space 406 and a machine readable descriptor in space 408.

Examining the label 404, a pharmacist will recognize that a descriptor has been provided in space 408 and therefore that an enhanced vial is required to store the medication prescribed in the order. In response to the indication that an enhanced vial is required the pharmacist retrieves an enhanced vial 400 and the printed label 404 and manually attaches the label 404 to the vial 400 as illustrated in FIG. 7.

Next, the pharmacist uses HHD 420 to read the descriptor in space 408. To this end the pharmacist positions reader 430 relative to space 408 so that the descriptor can be read. After the descriptor has been successfully read light 401 is activated for a short period to indicate completion of the reading. HHD 420 provides the descriptor information to server 202. Server 202 then accesses database 210 (see FIG. 2) and correlates the descriptor (e.g., an order number) with one of the orders in prescription order section 222 (see FIG. 3). Server 202 then retrieves the enhanced data from column 236 corresponding to the identified order and provides the enhanced data to HHD 420.

Continuing, the pharmacist next places HHD 420 in a position adjacent device 402 that allows HHD 420 to write information to device 402. In the case where device 432 and device 402 include electrical contacts actual contact between the contacts has to be made. In the case of RF transmission, placement of device 432 proximate and adjacent device 402 should suffice.

Next HHD 420 writes the enhanced information to device 402. After the data is written to device 402 light 403 on top of HHD 420 is activated to indicate that the data has been written. Although not illustrated it is contemplated that a triggering mechanism may be provided on HHD 420 to either start a reading process or start a writing process.

This embodiment ensures that the data written to an enhanced device (e.g., 402) corresponds to the information printed in human readable form.

Another version of this embodiment includes a system including a vial source selector that automatically selects the type of vial to be used to fill a prescription. To this end, referring to FIG. 9, an exemplary configuration 448 of this type includes an enhanced vials source 450, a standard vial source 452, a source selector 454, a label source 456, a print station 458, a descriptor reader 460 and a write/label station 462. Although not illustrated it should be understood that each of the components in configuration 448 are part of a print/write system (see 207 in FIG. 2) and are linked to a server 202 for control thereby.

Sources 450 and 452 each feed selector 454 which is equipped to select either enhanced or standard vials from the sources 450 and 452 depending upon instructions received from server 202. The selected vial is provided to the write/label station 462 for either, in the case of a standard vial, labeling or, in the case of an enhanced vial, writing and labeling. The completely specified vial is then provided at an output to a destination location identified by numeral 464.

Label source 456 is similar to the source in FIG. 6 including a string of accordion linked labels that can be drawn into print station 458 for printing human readable indicia thereon. The main difference in label sources is that source 456 includes labels having first and second spaces 406 and 408 (see FIG. 7) for printing human and machine readable indicia, respectively while source 240 only includes a space 52 for printing human readable indicia. Print station 458 includes a printer that prints the indicia corresponding to specific orders on labels, the labels provided to descriptor reader 460. As in the fourth embodiment described above, when an enhanced vial is required to store a medication, server 202 recognizes the requirement and prints a descriptor in space 408 that can later be used to identify that an enhanced vial is required and which order the label corresponds to in the order queue (see FIG. 3). In the alternative, when a medication user does not require an enhanced device 402, server 202 only causes human readable indicia to be printed in first space 406 and leaves space 408 blank or, to indicate that the system is working properly, may provide some other indicator in space 408 that is recognizable as an indication that a standard vial should be used to store the prescribed medication.

Reader 460 attempts to read information in each second space 408 (i.e., the machine-readable descriptor). The read information is provided to server 202 which determines, based on the information, which vial type should be used, standard or enhanced. Where a standard vial is required, server 202 causes source selector 454 to select the a standard vial from source 452 and provide the vial to write/label station 462. Station 462 receives each of the label that indicated a standard vial and the standard vial at the same time, attaches the label to the vial and then provides the vial at the destination location 464.

Where an enhanced vial is indicated by the descriptor in space 408, server 202 performs two tasks simultaneously. First, server 202 causes selector 454 to select an enhanced vial from source 450 and provides the enhanced vial to station 462. Second, sever 202 uses the descriptor information to identify the order in order section 222 that corresponds to the specific label. Once the order is identified, server 202 retrieves the data in the enhanced column 236 corresponding to the order. Server 202 then provides the retrieved data to write/label station 462 and print station 458 provides the label to station 462.

Next, when the vial, enhanced data and label are received at station 462, station 462 attaches the label to the vial and writes the enhanced information to the enhanced device 402 (see FIG. 7). The specified vial is then provided at destination location 464 for a pharmacist to place medication in the vial for storage.

Figure 9:
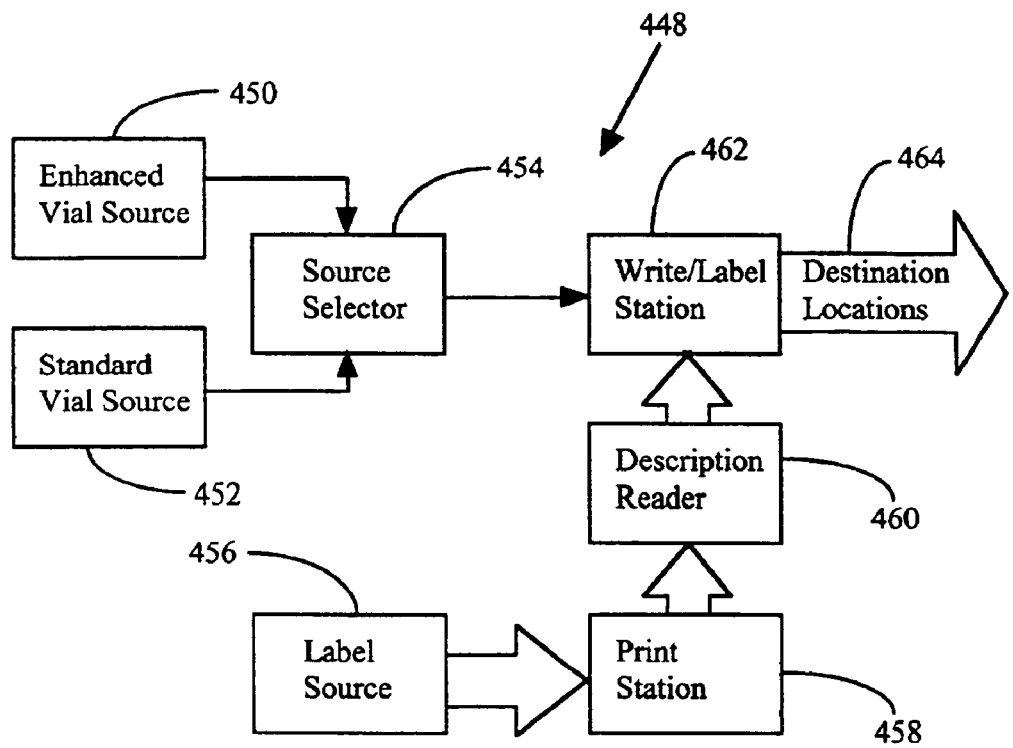
FIG. 9 is a schematic diagram of one inventive system.

Referring still to FIG. 9, one other similar version of the present invention would have a configuration similar to the configuration illustrated without descriptor reader 460. In this case, instead of determining two separate times that enhanced information is to be included on a device 402 as is necessary in the above example (i.e., one determination required to print the correct descriptor information in space 408 and a second determination required to identify the order corresponding to a label so that associated enhanced information can be retrieved), the determination need only be made once. To this end, when an order comes up in the queue 276, server 202 can identify any enhanced information in column 236 once that corresponds to the order and then can store that information in a memory buffer. Based on that information server 202 can cause selector 454 to select the appropriate vial type (i.e., enhanced or standard) can print the human readable indicia in space 406 and can sequence provision of the vial, the label and the enhanced information to write/label station 462 so that the enhanced and human readable information on the vial corresponds to the same order. In this case, instead of providing a label like label 404 having first and second spaces, a label more akin to label 302 in FIG. 6 may be more appropriate as the descriptor information need not be read from the label. Thus, in this case, the descriptor is the information in column 236 that corresponds to an order as opposed to information printed on a label.

FIFTH EMBODIMENT

A fifth embodiment of the invention is similar to the above embodiments except that the source for vials includes a mechanism for attaching enhanced devices to standard vials. For example, the device attacher may include a glue and pressing configuration, a plastic heat welding configuration, an ultra-sonic vibrating configuration or any other type of attaching configuration known in the art that is capable of forming a bond between an enhanced device and a vial.

Figure 10:
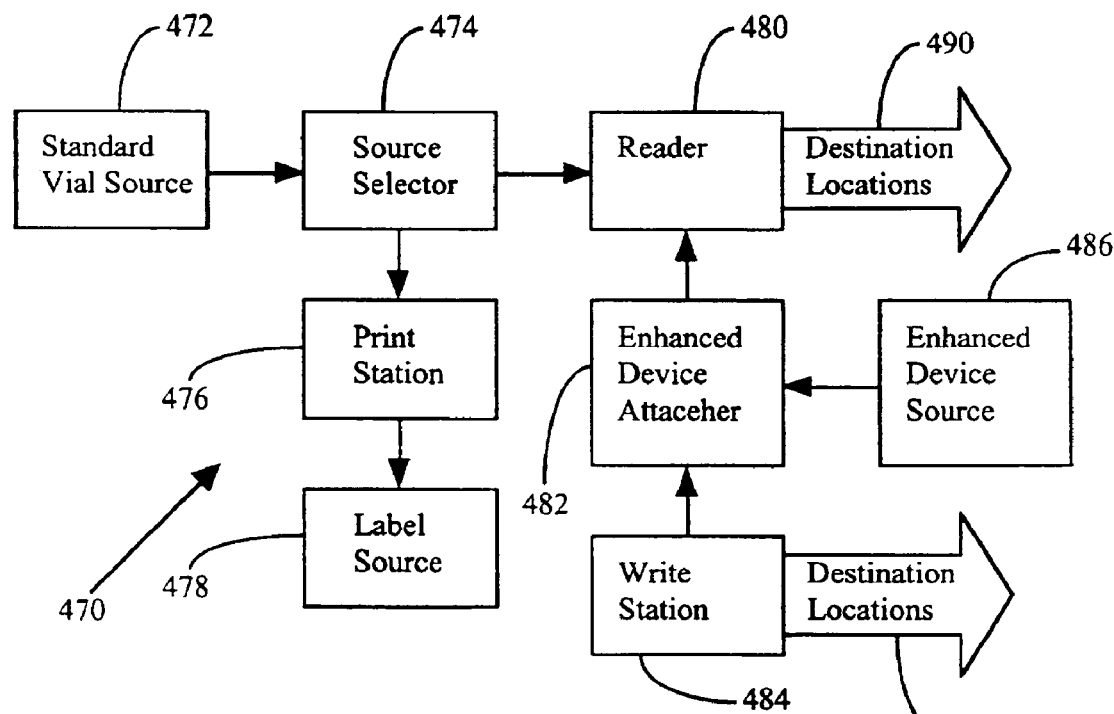
FIG. 10 is similar to FIG. 9, albeit of another inventive system.

In one version of this embodiment, referring to FIG. 10, a printing system 470 includes a standard vial source 472, a label station 474, a print station 476, a label source 478, a descriptor reader 480, an enhanced device attacher 482, a write station 484, an enhanced device source 486 and a destination location 490. Once again, in this embodiment, each of the system components is linked to a server 202 for control and sequencing. Vial source 472, label source 478, print station 476, label station 474 and descriptor reader 480 are similar to the components described above and therefore are not described again here in detail. Label source 478 is specifically a source to provide labels like label 404 in FIG.

7 having first and second spaces 406 and 408 for printing human readable information and a machine-readable descriptor, respectively.

Label source 478 feeds print station 476. Server 202 accesses orders in database 210 one at a time and determines if an enhanced vial is required for the medication prescribed in each order. For labels to be attached to standard vials that do not have an enhanced device, server 202 causes print station 476 to print human readable indicia in space 406. For labels to be attached to enhanced vials that include enhanced devices, server 202 causes print station 476 to print human readable indicia in space 406 and to print the machine readable descriptor in space 408.

The printed labels and standard vials are provided to label station 474 where station 474 attaches each label to a standard vial. The labeled vials are provided to reader 480.

Upon receiving a labeled vial, reader 480 attempts to read the descriptor in space 408 to determine if an enhanced device should be attached to the vial. Where no descriptor is printed in space 408 or a descriptor that indicates that no enhanced device is required is printed in space 408, server 202 causes reader 480 diverts the vial to destination location 490 for use by a pharmacist.

Where the descriptor in space 408 indicates that an enhanced device is required, server 202 causes reader 480 to provide the vial to enhanced device attacher 482. In addition, server 202 retrieves the enhanced data from database 210 corresponding to the order indicated by the descriptor and provides the enhanced data to write station 484. Enhanced device source 486 provides enhanced devices to attacher 482 and attacher 482 attaches a device to every vial received.

After a device is attached to a vial the vial is provided to write station 484 where station 484 writes the enhanced data to the enhanced device. The completely specified vial is then provided at location 490.

Referring still to FIG. 10, as in the case of the fourth embodiment it is contemplated that another version of the fifth embodiment may not include a reader 480 and instead, server 202 would control label station 474 to either provide vials to destination location 490 or to attacher 482 depending upon whether or not an enhanced vial or a standard vial were required. In this case, when an order comes up in queue 276 server 202 accesses the print information in column 234 and, if enhanced information exists in column 236, also accesses that information for the order. Both sets of information (i.e., enhanced and print) are stored in a server memory buffer.

Where no enhanced information corresponds to an order server 202 simply provides the print information to print station 476, controls label station 474 to attached printed labels to vials and also to provide the standard labeled vials to location 490. Where enhanced information corresponds to an order, server 202 provides the print information to print station 476 and provides the enhanced information to write station 484. In addition, after a label is applied to the vial at station 474, server 202 causes station 474 to divert the vial to enhanced device attacher 482. Again, attacher 482 attaches an enhanced device to every vial received.

The vials, including enhanced devices, are provided to writ station 484 that in turn writes the enhanced information to the enhanced device. The completely specified vials are then provided at location 490 for use by a pharmacist. In this case the label would not require a second space (i.e., 408 in FIG. 7) for printing the machine-readable descriptor as such a descriptor is no longer needed for correlating printed and written information on the vial.

Other versions of this embodiment are also contemplated. For example, instead of first attaching an enhanced device to a vial and second writing enhanced information thereto, the system may write the enhanced information and then attach the device to the vial.

Moreover, the system may not include an enhanced device attacher. In this case, the system may simply determine when an enhanced device is required, write enhanced information to the device and provide the enhanced device to a pharmacist for manual attachment to the vial. In such a system, however, it is important that the enhanced device and the labeled vial corresponding thereto be presented to a pharmacist at the same time so that the pharmacist can attach the device to the correct vial.

SIXTH EMBODIMENT

Figure 11:
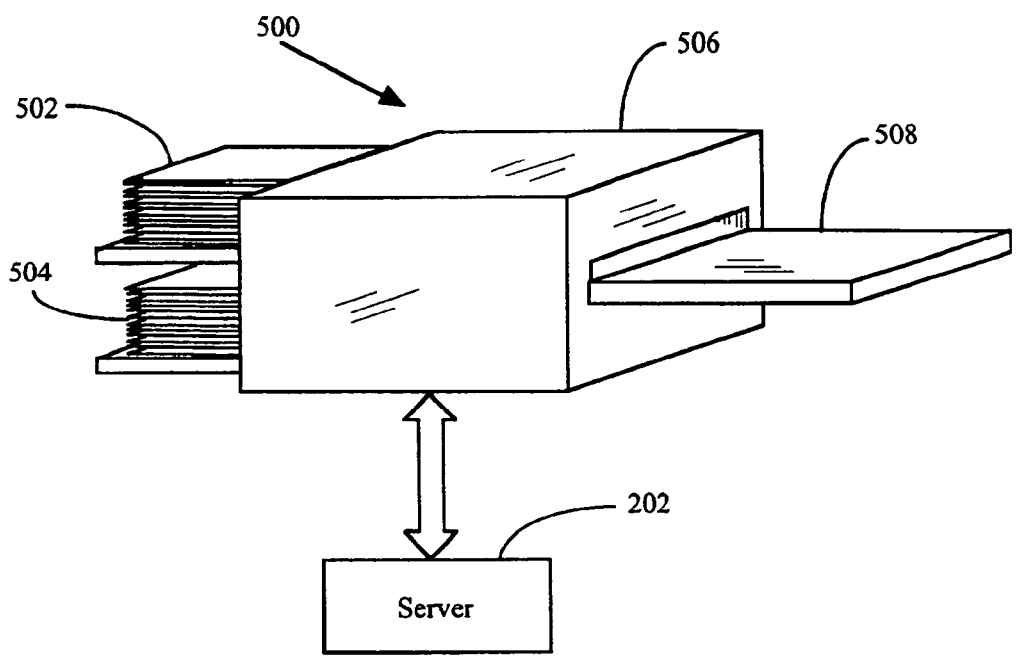
FIG. 11 is a perspective view of a printer system.
Figure 12:
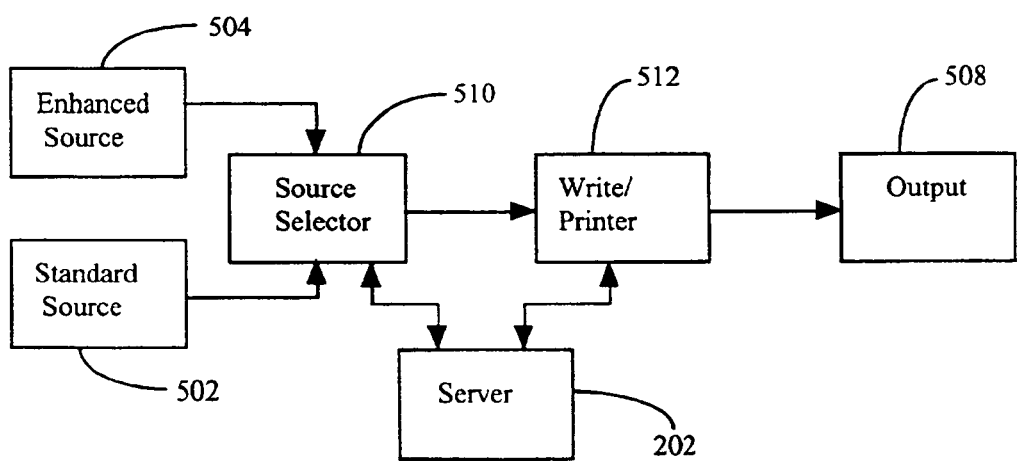
FIG. 12 is a diagram illustrating operation of the Printer system of FIG. 11.

Referring now to FIGS. 3, 11 and 12, a sixth inventive embodiment includes a specifying system 500 linked to server 202 for generating completely specified enhanced or standard labels, depending upon requirements of specific orders in order section 222 of database 210. Referring also to FIG. 1, in the system 500 illustrated is used to generate either labels like label 50 including a section 52 for printing human readable indicia and section 65 including a machine-readable device 69 or standard labels that only include human readable indicia (not illustrated).

In one embodiment specifying system 500 has an appearance similar to that of a conventional printing system having at least two supply source bays 502 and 504 that feed into a housing 506 that in turn generates product at an output or destination 508. Importantly, source bays 502 and 504 are use to provide labels of two different types. First bay 502 is stocked with standard type labels that do not include enhanced devices (i.e., the standard labels do not include devices 69) but that include a space for printing human readable indicia. Referring also to FIG. 1, second bay 504 is stocked with enhanced labels 50 that include both an enhanced device 69 and a space 52 for printing human readable indicia.

Referring still to FIGS. 11 and 12, housing 506 encloses both a source selector 510 and a writer/printer 512 that are linked to server 202 to facilitate sequenced control. Selector 510 is fed by each of sources 502 and 504 and is constructed so that the selector 510 can select a label from either one of bays 502 or 504, depending on requirements of specific orders. Selector 510 feeds labels to writer/printer 512.

Writer/printer 512 receives labels and writes information to enhanced devices 69 and prints information in the human readable indicia spaces on each label. In one embodiment printing and writing are performed simultaneously while in other embodiments writing and printing may be performed in a sequence. Fully specified labels are then provided at output destination bay 508 for manual attachment to standard vials by a physician either prior to or after medication is placed in the vials for storage.

Referring to FIGS. 1, 2, 3, 11 and 12, in operation, when an order (i.e., 001) comes up in queue 276 server 202 determines if there is any enhanced data in column 236 corresponding to the order and therefore determines which label type, standard or enhanced, is required for a particular order. As in the embodiments above the label-type determination step can be performed in any of several different ways. In this embodiment it will be assumed that whenever a standard label is to be used to identify a medication, a standard vial flag is provided in column 236 and when an enhanced label (i.e., one including a device 69) is to be used to identify a medication, the enhanced information is provided in column 236. Thus, the determining step includes retrieving the information in column 236 corresponding to an order and determining if the information includes enhanced data or a standard vial flag.

On one hand, when the retrieved information includes a standard vial flag server 202 retrieves the information in print column 234 corresponding to the order and then causes selector 510 to select a standard label from source 502. Server 202 provides the standard label and the print information to writer/printer 512. Writer/printer 512 prints the print information in the human readable indicia space 52. The printed (i.e., in this standard label case fully specified) label is then dispatched at destination output 508 for manual attachment.

On the other hand, when the retrieved information includes enhanced information server 202 retrieves the information in print column 234 corresponding to the order and causes selector 510 to select an enhanced label from source 504. Server 202 provides the enhanced label, the printed information and the enhanced information to writer/printer 512. Writer/printer 512 prints the print information in the human readable indicia space and simultaneously writes the enhanced information to device 69. The written and printed label is then dispatched at destination output 508 for manual attachment.

SEVENTH EMBODIMENT

This seventh embodiment is similar to the embodiments described above in that this embodiment facilitates automatic configuration of a container for a medication where the container configuration is a function of information to be included with the medication. However, instead of determining when an enhanced information storage device should be included with a container and when such devices are not required, this embodiment determines container size as a function of the amount of information to be included with the container or, more precisely, as a function of the amount of space required to accommodate human readable indicia to be included on the external surface of the medication container.

To this end, as indicated above, there is general information that is typically printed in human readable indicia on a basic label to be placed on the outside of each medication container including a medication users name, medication type, consumption requirements, prescribing physician, etc. The label space required to accommodate the a basic label including the typical information is generally the same for all prescriptions and therefore a single basic label size and shape can be used for such information.

However, in addition to the typical information, there is also often other information that is medication specific that must be included on medication containers. For example, many different brightly colored warning labels must often be included on vials to warn users of specific requirements. For instance, some labels indicate that medication should be taken on an empty stomach or with a meal or prior to a meal or in the morning or that the user should avoid prolonged sun exposure while taking the medication, etc.

In some cases the basic label including the typical information often will be sized so that the basic label takes up almost all of the space on the external surface of a small vial. In these cases, if additional warning labels are required, a larger vial having a larger external surface area is necessary to accommodate both the basic and additional warning labels.

Despite requiring additional surface area to accommodate all of the required labeling for a specific medication or prescription, sometimes a pharmacist will inadvertently select a vial that is too small to accommodate all of the basic and warning labels and will proceed to place a basic label thereon. Often this occurs when a pharmacist has not checked to determine which warning labels should be included on a vial until after the basic label is printed and applied. Because all of the basic information is important the pharmacist cannot place required warning labels over the basic labels and therefore the vial including the label has to be thrown away and a new larger vial has to be used. Obviously this mishap is wasteful and should be avoided.

According to this seventh embodiment of the invention, because all medication orders (e.g., see FIG. 3) include the basic information required for a prescription and the basic information indicates the medication type, when an order comes up in queue 276, server 202 can determine the medication type, identify which warnings should be included on the external surface of the vial, determine the surface areas required to accommodate each of the basic and warning labels, determine the total area required to accommodate all of the basic and warning labels, identify a vial type suitable (i.e., having sufficient external surface area) to accommodate the required area and then at least indicate the suitable vial type. In one embodiment the system would simply indicate the suitable vial type to a pharmacist, the pharmacist then selecting the indicated type. In other embodiments the system may be equipped with several vial sources (e.g., three sources), each source including a separate vial type, and a source selector similar to the selectors described above, capable of selecting the suitable vial type to be presented to the pharmacist.

According to another aspect of the invention instead of tying vial type to warning label and basic label area requirements, vial type may be tied to the volume of medication to be included in the vial. To this end characteristics regarding medications may be stored in a database that can be used to, based on medication type and order quantity, determine the volume of a required container. For example, medication tablet volumes for various medication types may be stored in the database such that the required volume for a quantity of medication (e.g., 100 tablets) can easily be determined as a function of table volume with some leeway to account for skewed stacking within the container.

According to yet other aspects of this embodiment a system processor or server may take into account both required medication volume and required basic and warning labels to determine container type.

OTHER ASPECTS

There are many other applications that can be used or facilitated with many of the inventive embodiments described above and that enhance the present invention. For example, there may be circumstances wherein a pharmaceutical company will provide interactive devices to users of particular medications to monitor medication consumption and symptoms during and after consumption.

For instance, assume that a pharmaceutical company A manufactures a new medication A that has been approved by the Food and Drug Administration and is being sold to cure a particular ailment. Also assume that since medication A has been on the market there have been a few reported incidents of adverse, but not life threatening, reactions to medication A but that no pattern from which reactions can be predicted has been established. To this end, almost all medication A users have no adverse reaction to medication A, some users have one adverse reaction type, other users have a second adverse reaction type and so on. Also assume that no pattern has been identified for how other medications (i.e., medications B, C, etc.) interact with medication A and affect the occurrence of adverse reactions. Moreover, assume that while not life threatening in the short run, some of the adverse reactions could cause long term effects and therefore, in some cases, when reactions occur, the medication A user should cease consumption to avoid subsequent physical problems.

In this case company A is clearly interested in monitoring medication A consumption circumstances and medication user reactions. For instance, it would be advantageous to be able to monitor user symptoms before and after medication A consumption, monitor other medications (i.e., medications B, C, etc.) consumed by the user, monitor periods between medication consumptions, be able to automatically determine if symptoms pose problems for a medication user, generate warnings for medication users, pharmaceutical companies, pharmacists and physicians and so on.

In addition to the circumstances detailed above assume that interactive devices for use with enhanced medication vials in this example include interface devices that enable device users to enter symptoms into the interactive devices and also are linkable via the Internet to company A's server so that information entered by each device user can be transmitted to and collected by company A's server. Once the server receives information from an interactive device, the server can perform any of several different contemplated algorithms to support one or more health safety functions (e.g., identify reactions and warn company A employees or the user's primary care physician, etc.).

In this case the technology to facilitate detailed feedback exists. In addition, it would clearly be in the pharmaceutical companies best interest to have all medication A users also be users of interactive devices and to have all medications that a medication A user consumes during the period of medication A consumption be dispensed into and stored in enhanced vials that can be read or that can transmit to the interactive devices. In fact, under these circumstances, while enhanced vials and interactive devices increase the costs associated with medicating, symptom feedback may be so valuable that company A is willing to fund or "sponsor" all costs of the enhanced vial and interactive system. In this case "sponsorship criteria" required for a sponsor to fund an enhanced device for a medication would simply be that one of the medications prescribed for the medication user be medication A.

Moreover, there may be other sponsoring entities such as a hospital that may require use of enhanced devices to ensure compliance. In this case, while the hospital may require the enhanced devices, some other entity such as an insurance company may actual fund the devices as a cost of medical services. Thus, while sponsorship often means that the sponsor is actually funding the devices, sponsorship can also simply mean that the sponsoring entity is only authorizing device use and that some other entity actually funds the devices.

Thus, whenever medication A is prescribed for a user, when a pharmacist fills the prescription, the prescription would be dispensed into an enhanced vial including an enhanced device. The pharmaceutical company or some other sponsoring entity (e.g., an insurance company) would provide required interactive devices to the pharmacy to be given to the medication user when the prescription is filled. The interactive devices would be equipped and programmed such that linking to the pharmaceutical server would be extremely simple (e.g., phone hookup with software to read enhanced device information from vials, organize the information, query for symptoms at appropriate times and report information back to the server).

Moreover, from medication A dispensation on and during consumption of medication A, the company A may also request that every subsequent medication prescription filled be placed in an enhanced vial, company A paying for the added cost of enhanced vials for all dispensed medications. In this manner all medications consumed during consumption of medication A would be logged by the pharmaceutical companies server along with symptoms and anomalies could be tracked and reported.

In addition to remote tracking and reporting to identify anomalies, it is contemplated that pharmaceutical companies and even pharmacies may be willing to fund interactive systems and enhanced devices to support other important health safety functions (i.e., avoid consumption of contra-indicated medications, ensure temporal relationships between consumption of specific medications, etc.). For instance, in the case of a pharmacy, providing interactive/enhanced device systems free of charge may be a selling feature to ensure that customers use your pharmacy routinely thereby increasing profits.

To facilitate automatic reporting and other health safety functions the present invention contemplates a method whereby a pharmaceutical company or other interested entity that funds or sponsors an interactive/enhanced system for medication users can cause all medications that meet sponsorship criteria, are subsequent to prescription of a certain medication and that are dispensed during consumption of that medication, to be dispensed into enhanced vials.

To this end at least a sponsored medication profile database is necessary that indicates all criteria required by the sponsor for the sponsor to fund the enhanced containers. Referring to FIG. 15, an exemplary sponsored medication profile database 664 includes a list of sponsored medications, criteria for sponsorship and corresponding sponsored functions. Database 664 includes a medication column 666, a criteria column 668, a sponsored functions column 670, a duration column 665, a sponsor column 672 and a rule # column 667.

Medications column 666 lists each sponsored medication (e.g., medications A, B, E, etc.) in a global sense (i.e., list 664 is medication user independent). Column 668 lists the criteria upon which a medication will be sponsored by a particular sponsor.

Column 670 lists the functions sponsored by the sponsor of a particular medication in column 666 and column 672 lists the entity (e.g., a pharmacy, a pharmaceutical company, etc.) that sponsored the medication and that should be billed for the enhanced devices and perhaps also the interactive devices required by user prescribees. To this end column 672 typically would include a sponsor's name, a billing address and other information such as, perhaps an e-mail address so that billing or invoice information could be generated and sent directly upon contain configuration.

Database 664 is preferably stored on a central database accessible to many pharmacy servers so that database information can be centrally entered and maintained. Thus, referring to FIG. 2, in this explanation it will be assumed that the database 210 is a remote clearinghouse database including at least the sponsored medication profile database 664.

It is contemplated that database 664 will be a work-in-progress so that medications will be added and removed and other information in the list will be modified from time to time by a pharmaceutical administrator or the like. Thus, when a database administrator determines, based on business or other objectives, that a medication should be added to the database or that some other information should be altered, the database is modified accordingly.

Referring still to FIG. 15, to simplify the task of forming and maintaining the sponsored medication database 664, it is contemplated that a database server will include software capable of instantiating one or more sponsored medication profiles whenever a database administrator specifies a new rule. For example, referring also to FIG. 2, assume that server 202 and interface 206 are useable to specify a new sponsored medication profile and that the new profile is to indicate that each of medications A, B and C will be sponsored any time medications A and B are prescribed for a user during the same time period (i.e., simultaneous consumption of medications A and B).

In this case, when the profile is specified, server 202 generates three separate sponsored medication profiles, a separate profile for each of medications A, B and C. The created profiles for this example correspond to rows 750, 755 and 757 in FIG. 15. To identify profiles that are related to each other a sponsorship rule number is provided for each profile in rule # column 667. The rule numbers for related profiles are identical (e.g., number 001 is indicated for each of related profiles 750, 755 and 757).

Thus, specification of a single sponsorship results in a first profile 750 indicating that medication A is sponsored if medication B is prescribed for a user, a second profile 755 indicating that medication B is sponsored if medication A is prescribed and a third profile 757 indicating that medication C is sponsored if both medications A and B are prescribed for a patient.

In one special case where a sponsor wishes to sponsor all medications when a particular medication is prescribed, two profiles are generated when the sponsorship is specified by a database administrator. To this end assume that company A wants to sponsor all medications prescribed for a user when medication A is prescribed. In FIG. 15 one profile 680 is generated for medication A and the criteria is listed as "none" (i.e., there is no criteria so that any time medication A is prescribed the medication will be dispensed into an enhanced vial). The second profile is an omnibus profile 780 that indicates that "All" medications are to be sponsored whenever medication A is prescribed (i.e., medication A is the criteria in column 668 corresponding to all other medications).

The rule numbers in column 667 can be used to eliminate existing profiles when a related sponsorship is to be discontinued. For instance, in the example above, when company A decides to discontinue sponsorship of medications A, B and C pursuant to rule number 001 (i.e., medications A, B and C will no longer be sponsored even when medications A and B are simultaneously prescribed), the database administrator can simply indicate that the corresponding rule is no longer valid thereby causing server 202 to eliminate all profiles having rule #001 in column 667.

In addition to the medication profile database 664, it is contemplated that, for at least certain embodiments of the invention circumstantial information other than information provided in a typical prescription may be required as criteria for sponsorship. For this reason, in these cases a second database referred to as a user characteristics profile is also remotely stored and maintained.

Figure 14:
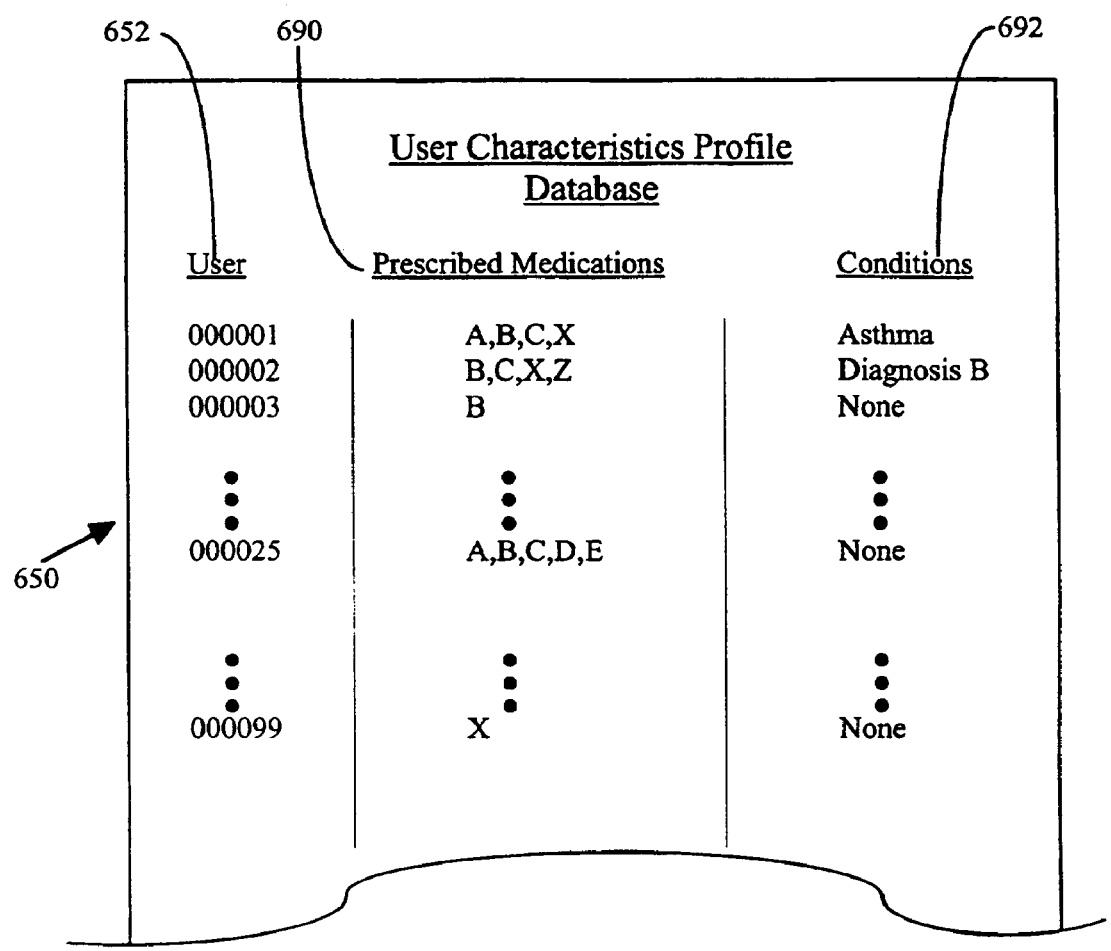
FIG. 14 is a sponsored medication profile database useable in the process of FIG. 13.

Referring to FIG. 14, an exemplary user characteristics profile database 650 is illustrated. Database 650 includes a plurality of correlated information columns including a user column 652, a prescribed medications column 690 and a conditions column 692. The user column 652 lists all medication users that are entered into the system. The prescribed medications column 690 lists all medications currently prescribed for corresponding medication users in column 652. For example, in FIG. 14 medications A, B, C and X are listed as currently prescribed for medication user 000001 while medications B, C, X and Z are listed as currently prescribed for user 000002.

Conditions column 692 includes a list of on going medical conditions or habits that may affect the medical condition of each medication user in column 652. For instance, column 692 indicates that user 000003 is a smoker and a heavy drinker, user 000001 has asthma and user 000002 has no medically important conditions. All of the information corresponding to each of the users in column 652 is referred to the user's prescription/condition (PC) profile hereinafter. For instance, the PC profile for user 000001 includes prescribed medications A, B, C and X and the asthma condition.

Figure 13:
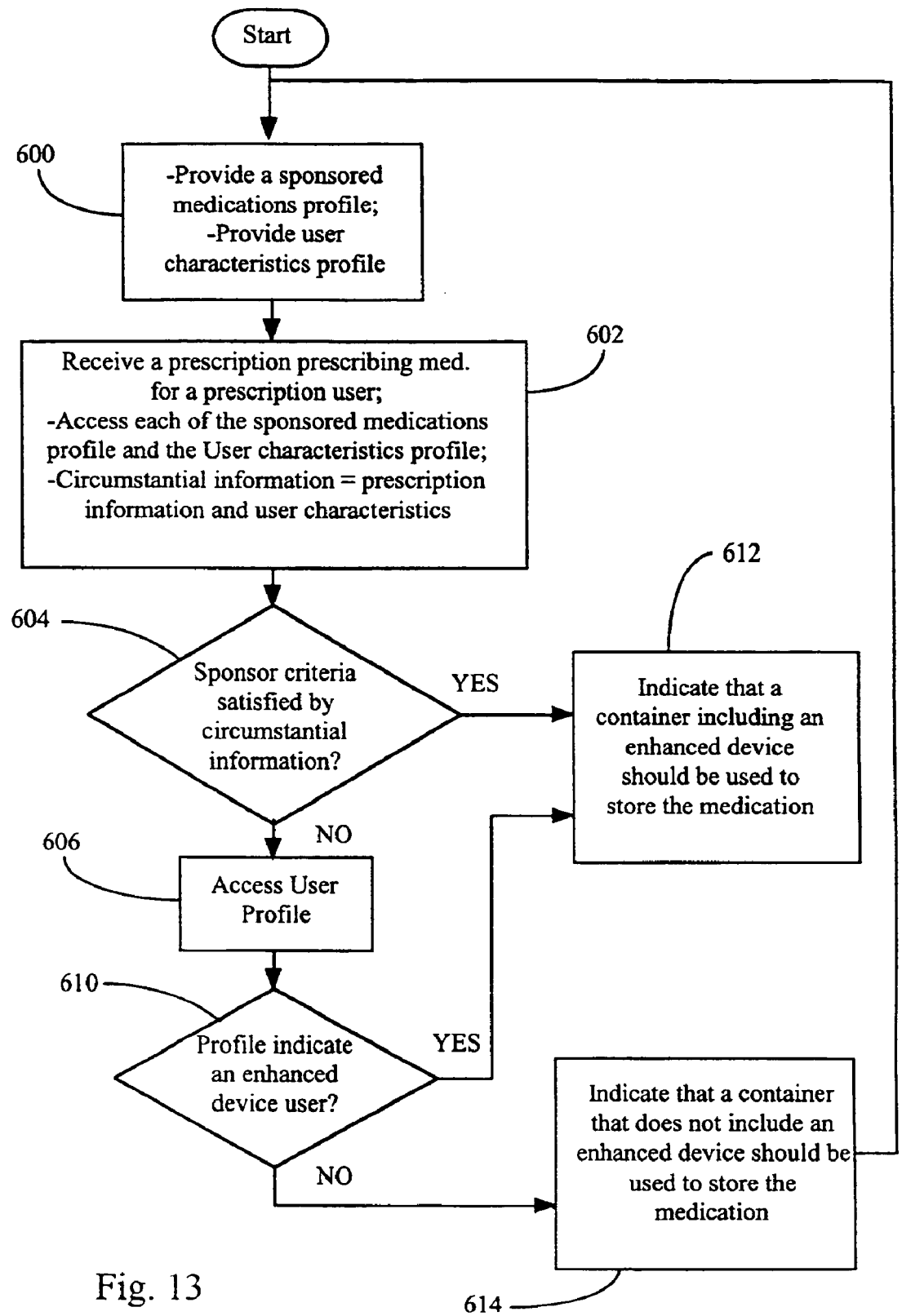
FIG. 13 is a flow chart illustrating a method whereby sponsorship for enhanced devices may be confirmed.

Referring now to FIGS. 13, 14 and 15, according to an exemplary inventive method, starting at block 600 in FIG. 13, a system user provides or provides access to the sponsored medication profile database 664 and also to the user characteristics profile database 650. Referring also to FIG. 2, with at least one sponsored medication profile formed and stored in clearinghouse database 210, at block 602 a prescription is entered by a pharmacist using terminal 206. The prescription information entered includes the medication prescribed, identification of the user (i.e., a prescription user) for which the medication was prescribed and perhaps other prescription type information such as consumption requirements, prescribing physician information, the diagnosis for which the medication has been prescribed, etc.

At block 602, when server 202 receives the prescription information, server 202 accesses the remote database 210 and retrieves sponsored medication profile database 664. Next, at block 604, for the prescribed medication, server 202 determines if there are any sponsored medication profiles. For instance, in FIG. 15 there are three sponsored profiles corresponding to medication A (see rows 680, 750 and 751), three profiles corresponding to medication B (see rows 682 and 752 and also the omnibus row 780) and so on. Where there is at least one sponsored profile related to the prescribed medication server 202 retrieves the profile criteria from column 668.

With profile criteria retrieved, at decision block 604 server 202 compares the sponsored profile criteria to combined information from the prescription and the user characteristics profile corresponding to the user for which the medication was prescribed. The combined prescription and user characteristics information is referred to generally as the circumstantial information related to the prescription. Where the circumstantial information does not satisfy a sponsored medication profile, server 202 control skips to block 606 where server 202 accesses a user profile (e.g., see 220 in FIG. 3) for the user. At block 610 server 202 determines if the user is already an interactive device user (i.e., owns and uses an interactive device for use with enhanced containers). Where the prescription user is not an interactive device user control passes to block 614 and server 202 indicates, via terminal 206, that a non-enhanced container should be used to store the prescribed medication.

Referring again to decision block 610, where the prescription user is an interactive device user control passes to process block 612 where server 202 indicates, via terminal 206, that an enhanced container should be used to store the prescribed medication. After an indication at either of blocks 612 or 614 control passes back up to block 600 where the process is repeated with the next prescription to be processed.

Referring once again to decision block 604 and to FIG. 15, where the circumstantial information satisfies a sponsored medication profile and therefore a sponsor has elected to provide interactive devices and enhanced devices for medication users meeting the criteria, control passes to block 612 where server 202 indicates via interface 206 that the medication should be dispensed into an enhanced container.

The above general concepts can best be understood by way of several examples. In a first example, assume a sponsor elects to sponsor all medications and functions when medication A is prescribed. Thus, wanting to track how medication A interacts with all other medications, company A elects to fund enhanced devices for all medications. Also assume the period of sponsorship is until cancelled (UC) and independent of other user conditions.

Referring again to FIG. 15, in sponsored medication profile 664 the specified rule results in two separate profiles 680 and 780 (i.e., the omnibus profile). In profile 680 the criteria for sponsorship of medication A in column 668 is "none" (i.e., every time, independent of condition, medication A is sponsored). Profile 780 indicates that all other medications are to be sponsored every time medication A is prescribed. The durations in column 665 are UC (i.e., until changed) and the sponsoring company is identified as company A for medication A and for all other medications.

Referring still to FIGS. 2, 13, 14 and 15, with the sponsorship criteria 680 specified in the sponsored medication profile 664 for medication A at block 600, after a prescription for medication A for user 000001 is received, server 202 accesses database 664 and identifies the prescribed medication as matching the medication in column 666 corresponding to each of profiles 680, 750 and 751 at block 604. Continuing, at block 604 server 202 begins with the first profile (i.e., profile 680) including a medication that matches the prescribed medication and determines if the criteria in column 668 are met. Where the criteria are not met server 202 steps to the next profile (i.e., 750) including a medication that matches the prescribed medication and determines if the criteria are met.

In some cases, as in the case of profile 750, where information in addition to the prescription information is required to determine if the criteria have been met, server 202 accesses user characteristics database 650 to obtain additional circumstantial information for comparison to the profile criteria. This process continues until either the circumstantial information (i.e., the prescription and characteristic information) for a profile satisfy the sponsorship criteria or all of the profiles have been compared to the circumstantial information without satisfaction. In the present example, referring again top profile 680, because profile 680 includes no criteria in column 668, contort simply passes to block 612 and server 202 indicates that an enhanced container should be used.

In a second example, assume a sponsor B that manufactures medication B elects to sponsor medication B (and no other medications) only when medication B is prescribed to address a specific diagnosis B and not when prescribed for other diagnosis. Also assume that company B only wishes to sponsor medication B during a one-year window from Jan. 1, 2001 to Jan. 1, 2002. Moreover, assume there are 10 separate health safety functions that may be sponsored and that company B only elects to sponsor function 2, 4 and 7.

Referring again to FIG. 15, row 682 includes sponsorship criteria corresponding to the present example. In row 682 the criteria include diagnosis B in column 668, the sponsored functions column 670 indicates functions 2, 4 and 7, the duration column 665 indicates the sponsored dates (Jan. 1, 2001 through Jan. 1, 2002) and the sponsor column indicates that company B is the sponsor.

Thus, referring to FIGS. 2, 13, 14 and 15, with the sponsorship profile 682 specified in the sponsored medication profile 664 for medication B at block 600, after a prescription for medication B is received for user 000002, server 202 accesses database 664 and identifies the prescribed medication as matching each of profiles 755 and 682. Beginning with the first profile 755, server 202 determines if the profile criteria is satisfied by the prescription information and other user information from the characteristics profile for user 000002 in database 650. Assuming profile 755 is not satisfied server 202 steps onto profile 682 and attempts to satisfy corresponding criteria (i.e., Diagnosis B in column 668). Assuming diagnosis B was specified as part of the prescription, profile criteria is met and server 202 indicates an enhanced container at block 612 (unless the date is outside the duration specification of Jan. 1, 2001–Jan. 1, 2002).

In a third example, assume a sponsor C that manufactures medication C elects to sponsor only medication C and only when medications C and D are prescribed together and does not want to sponsor any other medications. Also assume that company C only wishes to sponsor until an affirmative change order changes the sponsorship status (i.e., the status is unless changed UC). Moreover assume that all health safety functions are to be supported.

Referring again to FIG. 15, row 686 includes sponsorship criteria corresponding to the present example. In row 686 the criteria include prescription of medication D in column 668, the sponsored functions column 670 indicates "all" functions (i.e., all functions are supported), the duration column 665 indicates UC, and the sponsor column indicates that company C is the sponsor.

Thus, referring to FIGS. 2, 13, 14 and 15, with the sponsorship criteria 686 specified in the sponsored medication profile 664 for medication C at block 600, after a prescription for medication C is received for user 000025 where medication D has already been prescribed for user 000025 (see FIG. 14, row 781, server 202 accesses database 664 and identifies the prescribed medication as matching the medication in profile 757 at block 604. Continuing, server 202 identifies criteria D in column 668 and then accesses database 650 to determine if criteria D (i.e., prescription of medication D) is satisfied for user 000025. In column 690 criteria D is satisfied and therefore control passes to block 612 and server 202 again indicates an enhanced container.

It should be appreciated that many other sponsorship criteria are contemplated, many additional health safety functions are contemplated and many additional combinations of sponsored secondary medications are contemplated by the present invention. For instance, one criteria may include a user's habits such as smoking or drinking or concern a user's environment (i.e., working in a noisy environment, a particularly polluted environment, etc.). In these cases, as many of these criteria may not be included along with a conventional prescription and may not be included in the user characteristics profile database 650, server 202 may be programmed to poll a pharmacist via interface 206 to gather required criteria information.

For instance, when a sponsorship criteria corresponding to a primary medication D is that the medication user must be a smoker and a prescription specifying medication D is received by server 202, server 202 may query the entering pharmacist to ask the user whether or not the user is a smoker. When the answer (i.e., yes or no) is provided via interface 206 to server 202, server 202 can then compare the primary medication-answer to the sponsorship criteria in database 664 and determine how to proceed. Thus, in some cases it is contemplated that database 664 will include queries to be presented to the prescription entering pharmacist as does sponsorship criteria corresponding to profile 690 for medication D in FIG. 15. The question regarding smoking along with a criteria key (i.e., a key indicating that if the answer is "yes", the criteria has been met) for the answer may be provided as "question 1" in column 668.

In another aspect, instead of storing a user's characteristics profile on a remotely accessible database, the profile could be stored on a personal device such as a personal digital assistant (PDA) or on a smart card so that a user could maintain control of his profile and present his profile to any pharmacy. For example, each time a medication is prescribed for a patient, the prescription may be indicated in the user's PDA. The PDA may also include a flag to indicate whether or not the user uses interactive devices and thus whether or not the user requires an enhanced vial. Upon filling a prescription a pharmacist can then use the PDA information to determine vial type.

In addition, the PDA may be equipped to indicate only specific medications to be dispensed into enhanced vials, to determine which medications to be dispensed into enhanced vials or to cooperate with a pharmacy server to determine and indicate which medications to be dispensed into enhanced vials. Thus, the PDA may be equipped to perform many of the function described above as being performed by the pharmacy server 202 or to cooperate with the server to facilitate the container specifying/configuring functions and to this end may include a small sponsored medications profile database.

Yet one other aspect of the present invention includes rendering billing information as a function of the container or vial type decision. To this end, when an interactive/enhanced storage system is sponsored by a pharmaceutical company, pharmacy or the like, the system may automatically determine which of several different entities should be billed for interactive/enhanced system hardware and services and then may automatically bill the appropriate entity. For instance, assume that a pharmaceutical company only wants to provide alerts and consumption record health safety functions where both medications A and B are consumed and only for medications A and B but that a medication A and B user wants to have alert and record functionality for each of medications A, B, C, D and E. In this case server 202 can ensure that each of medications A through E be dispensed into enhanced vials, that the extra costs associated with medications A and B be billed to the pharmaceutical company and that the extra costs associated with medications C, D and E be billed to the medication user.

In another aspect of the invention many of the concepts described above regarding sponsorship may be combined with other concepts regarding actual provision of enhanced devices, enhanced labels or enhanced containers. For instance, where server 202 determines that an enhanced device has been sponsored, in addition to indicating an enhanced container, where server 202 is linked to a container source or a label source or an enhanced device source, server 202 can cause an enhanced container configuration to be provided to the pharmacist. In this regard the medication profiles in database 664 may further include instructions regarding information to provide on the enhanced devices, information to be printed in human readable form on each container, programs to run to perform the sponsored functions, billing information and so on.

Referring now to FIG. 16, an inventive label printing sheet 520 is illustrated. Referring also and again the FIGS. 11 and 12, a stack of sheets 520 may be provided at enhanced source 504 so that whenever an enhanced label (i.e., a label including a memory and/or a processor) is required, server 202 causes writer/printer 512 (see also FIG. 12) to select a sheet 520 from source 504.

In at least one embodiment sheet 520 is in sticker form including the illustrated printing surface having an adhesive coating 526 (see also FIG. 17) on a rear label face that adheres to a plastic or paper backing (not illustrated) for easy removal. The illustrated surface is printable via a conventional workstation printer.

Sheet 520 includes two sections, a printing section 524 and a label section 527. Printing section 524 is provided so that information regarding a prescription may be generated for review by a pharmacist or for use by a medication user. For example, in addition to the information that may be printed on a label, additional and more detailed information may also be printed such as instructions for the medication user, information about the prescribing physician, information regarding the user's allergies, information regarding how to use the label in section 527, etc.

Label section 527 includes an enhanced label 50 formed in sheet 520, a score being provided about the outer edge of label 50 so that label 50 can easily be removed from the sheet 520 backing member. Once removed, as with conventional sticker type labels, the adhesive 526 on the rear label face is used to stick the label to a vial or some other container.

Label 50 is formed with a very specific shape that is configured to aid a person in placing the label on a particularly shaped container and is especially useful where an enhanced device is used in conjunction with some other information reading device. To this end, where an enhanced reading device includes an upwardly facing surface for supporting a container including medication it has been recognized that the enhanced device should be positioned on the undersurface of the container. Nevertheless, because most medication containers extend upward (e.g., a vial), it is advantageous to provide the printed section of a label on a laterally visible side of the vial.

To facilitate placement of the printed and enhanced sections of label 50, the label has a main section 527, a connecting portion 528, and a bottom portion 529. Label 50 in FIG. 16 has the enhanced device 69 positioned in bottom portion 529. Device 69 includes a processor and some type of power source. The power source may be a battery or perhaps an RF coil that receives energy from a magnetic field proximate the device 69. Conductors 530 extend from enhanced device 69 to an indicator 532 in main section 527.

Indicator 532 may be any of several different indicator types. One indicator type is a disposable pre-screened LCD like the devices commonly used on the sides of batteries to indicate battery charge. A typical pre-screened LCD includes a message on a message surface 533, a transparent plastic sheet there over such that a gap is formed between the sheet and message surface 533, liquid crystal material within the gap and two electrodes disposed on opposite ends of the gap. When no voltage is applied between the electrodes, the liquid crystal remains opaque and the message on the message surface cannot be observed. However, when a voltage is applied between the electrodes, the liquid crystal becomes transparent and the message there below becomes observable.

In the present case the message on surface 533 instructs a medication user to "Take Med". Thus, when indicator 532 is activated it becomes transparent revealing the "Take Med" message instructing the user to consume medication. The processor within enhanced device 69 may control operation of indicator 532 to indicate when a medication should be taken. In other words, with a medication regimen stored in device 69, the processor tracks time and when a prescribed time to take a medication occurs, the processor causes the indicator to indicate that medication should be consumed.

Referring still to FIG. 16, if bottom portion 529 is removed from main section 527, conductors 530 will be cut preventing indicator 532 from functioning. In some embodiments of the invention the indicator 532 is may not be provided. Nevertheless, it is contemplated that conductors 530 may still be provided so enhanced device 69 can detect tampering, e.g. by opening a circuit tied to memory cells preventing the memory cells from being read. This anti-tampering feature provides a useful way to prevent a label 50 from being moved from one vial 20 to another. The anti-tampering feature can be enhanced by designing connecting portion 528 so as to be easily torn if any attempt is made to remove a section of the label 50 from vial 20.

Main section 527 includes two different printable sections including a main printing section 52 and a plurality of safety flags 534. Main printing section 52 is provided to accommodate typical prescription information such as an indication of medication type and also simple information regarding medication regimen such as "Take two tablets three times daily". Safety flags 534 can be selectively printed with safety text (represented by lined 536) and can be removed along with main printing section 52 when needed for application to vial 20 (i.e., a subset of the safety flags may be removed).

Referring now to FIG. 17 another embodiment of label 50 is illustrated including an enhanced device 69 coupled by conductors 530 to a plate sensors 538. Sensor 538 may be part of a capacitive or RF memory reading circuit such as a Motorola BiStatix™ device.

FIG. 18 shows label 50 attached to vial 20 showing main section positioned on a vertical wall of the vial 20 and bottom portion 529 attached to the bottom 24 of vial 20. This arrangement is particularly desirable when bottom 24 and the attached enhanced device is to be placed on a corresponding reading sensor of an interactive medication monitoring device. To this end, an RF sensor (not shown) could be provided that may support one or more vials with devices on the undersurfaces. The sensor may be able to sense that a vial is on the sensor surface and read information including regimen information, from the enhanced device. Thereafter, a processor linked to the sensor may track time and, when a regimen time to consume medication occurs, the processor may either indicate that the medication should be consumed or may cause indicator 532 to indicate required consumption. To this end, the processor may send energy to the vial via the RF sensor causing the indicator to become transparent.

Figure 19:
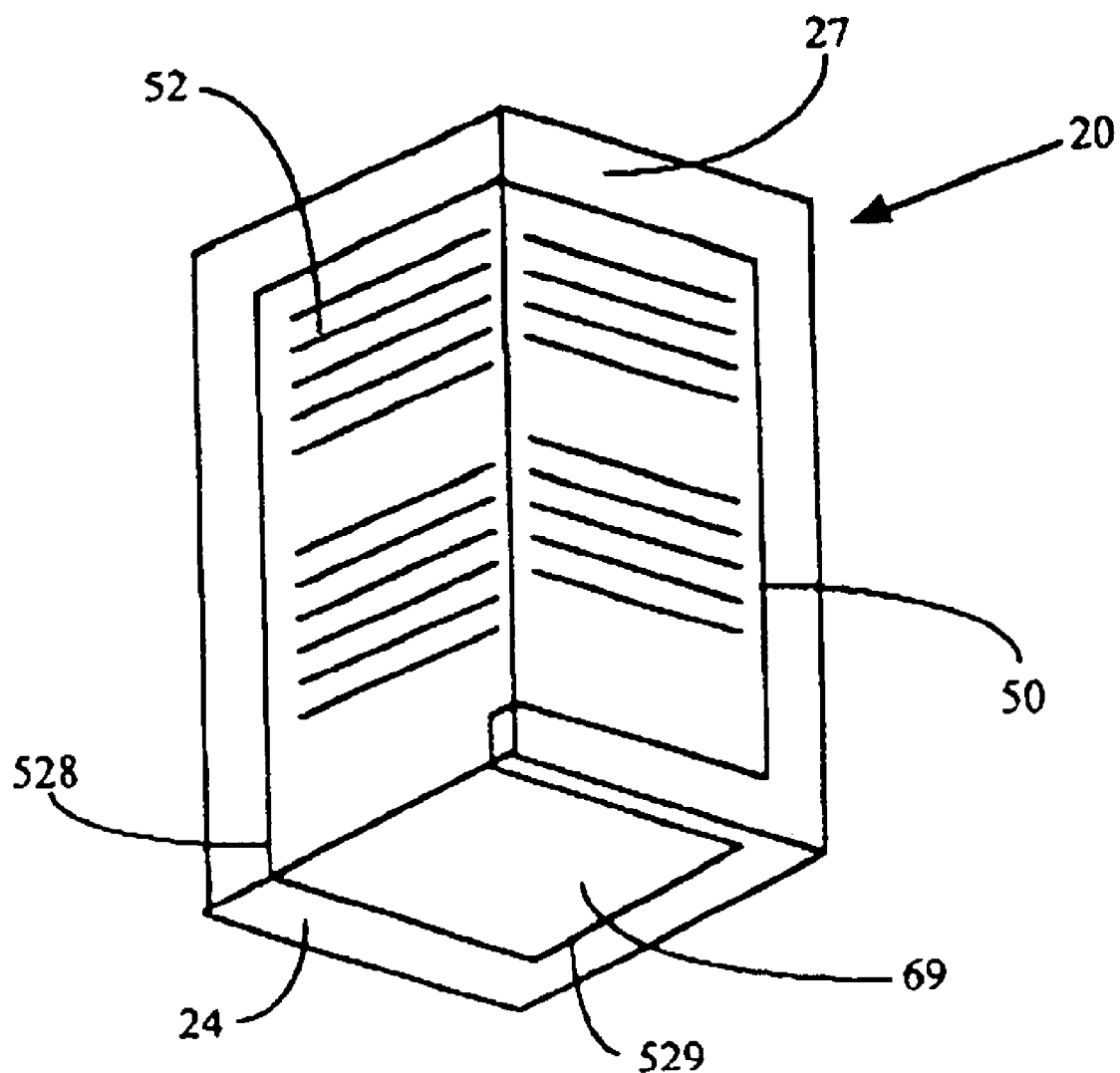
FIG. 19 is a perspective view of another inventive label similar to the label illustrated in FIG. 18.

Other arrangements for label 50 are contemplated (see FIG. 19) so as to make it easy for a pharmacist to dispense medication and attach a label 50 to a vial 20 to ensure the enhanced device 69 is placed on the under surface of the vial 20. For a vial with a square cross section label 50 may be as arranged as a single rectangle without a connecting portion (i.e., without section 528). To aid the pharmacist in correct placement of label 50 on vial 20, bottom portion 528 may be a different color or texture.

It should also be understood that the enhanced label may include a memory with any combination of processor, indicator, & a power source as part of the enhanced label. To this end it has been recognized that each of processors, indicators and power sources are becoming less expensive and more versatile and therefore that each may become disposable (i.e., relatively inexpensive).

It should be understood that the methods and apparatuses described above are only exemplary and do not limit the scope of the invention, and that various modifications could be made by those skilled in the art that would fall under the scope of the invention.

To apprise the public of the scope of this invention, the following claims are made:

What is claimed is:

1. An apparatus for configuring an indicating configuration to be associated with a container wherein each indicating configuration includes an indicator and data stored thereon related to an order associated with the container and at least a sub-set of indicating configurations include an enhanced memory device and enhanced data stored thereon, an enhanced device being a device that cooperates with a data collector to gather information therefrom, at least one descriptor associated with each order that can be used to identify the indicating configuration and the data to be stored via the indicating configuration, the apparatus comprising:

a reader for reading each descriptor;

a writer for writing data to enhanced devices; and a processor linked to the reader for receiving each descriptor and using the descriptor to identify when enhanced data is associated with an order, the processor, when enhanced data is associated with an order, causing the writer to write enhanced data to an enhanced device and, when enhanced data is not associated with an order, causing another indicating function to be performed.

2. The apparatus of claim 1 further including a database correlating descriptors with associated data to be written to enhanced devices, the processor linked to the database and, when a descriptor is received, identifying by accessing the database and determining if enhanced data corresponds to the specific descriptor.

3. The apparatus of claim 2 wherein the database includes an order queue including a plurality of orders, each order including a descriptor, the reader including a queue pointer that sequentially identifies each of the descriptors in the queue and provides the descriptors to the processor.

4. The apparatus of claim 3 wherein each container is a medication container, each order is a medication prescription for a particular medication user and the data is data related to the medication to be stored in the container.

5. The apparatus of claim 4 wherein the data is also a function of a medication user corresponding to the order.

6. The apparatus of claim 1 wherein at least a sub-set of the descriptors indicate that no data should be written to an enhanced device and wherein the another function includes disabling the writer when no data is to be written to an enhanced device.

7. The apparatus of claim 1 further including a container source controlled by the processor and providing containers having enhanced devices attached thereto.

8. The apparatus of claim 7 wherein at least a sub-set of the descriptors indicate that no data should be written to an enhanced device and wherein the another function includes disabling the writer when no data is to be written to an enhanced device.

9. The apparatus of claim 7 wherein the container source includes an enhanced container source and a non-enhanced container source for providing enhanced and non-enhanced containers, respectively, and wherein, when a descriptor indicates that no data is to be written to an enhanced device, the another function includes causing the non-enhanced source to provide a non-enhanced container.

10. The apparatus of claim 9 wherein the enhanced container source includes an enhanced device source and a device attacher, the attacher receiving non-enhanced containers and, when an enhanced container is required, attaching an enhanced device to a container to provide the enhanced container.

11. The apparatus of claim 10 wherein the processor also uses the descriptor to identify human readable indicia related to the order and the apparatus further includes an indicia printer for printing the indicia for inclusion on the container.

12. The apparatus of claim 11 further including a label source for providing labels and wherein the printer prints the indicia on the label.

13. The apparatus of claim 12 further including a label attacher for attaching the labels to the containers.

14. The apparatus of claim 10 wherein the enhanced devices are attached to labels and wherein the attacher attaches by attaching the labels to the container.

15. The apparatus of claim 14 wherein the processor also uses the to identify human readable indicia related to the order and the apparatus further includes an indicia printer for printing the indicia on the label.

16. The apparatus of claim 1 further including a label source controlled by the processor and providing labels having enhanced devices attached thereto for inclusion on the containers.

17. The apparatus of claim 16 wherein the another indicating function includes disabling the writer.

18. The apparatus of claim 17 wherein the label source includes an enhanced label source and a non-enhanced label source for providing enhanced labels including enhanced devices and non-enhanced labels, respectively, and wherein, when a descriptor indicates that no data is to be written to an enhanced device, the processor causes the non-enhanced source to provide a non-enhanced label.

19. The apparatus of claim 18 wherein the enhanced label source includes an enhanced device source and a device attacher, the attacher receiving non-enhanced labels and, when an enhanced label is required, attaching an enhanced device to a label to provide the enhanced label.

20. The apparatus of claim 19 wherein the processor also uses the descriptor to identify human readable indicia related to the product to be stored in the container and further including an indicia printer for providing the indicia on the label.

21. The apparatus of claim 1 wherein the processor also uses the descriptor to identify human readable indicia to be included on the container wherein the indicia is related to the order, the apparatus further including a label source and an indicia printer linked to the processor, the processor sequencing the indicia printing and data writing such that indicia and data corresponding to the same descriptor are provided on the same container.

22. The apparatus of claim 21 wherein each label includes an indicia surface and an attached enhanced device and wherein the printer and writer print and write the indicia and data corresponding to a single descriptor to the surface and device, respectively, at the same time.

23. The apparatus of claim 21 wherein each of the writing and printing steps is a specifying step and each of the indicia and data are specifying information, a first of the specifying steps occurs before a second of the specifying steps, each printing and writing cycle is a specifying cycle, for each descriptor, the first step occurs N specifying cycles prior to the second step and the processor sequences the second step specifying information to be specified N cycles after the first step specifying information is specified.

24. The apparatus of claim 23 wherein N is 1.

25. The apparatus of claim 1 further including a container source wherein the source provides containers with attached descriptors.

26. The apparatus of claim 25 wherein the descriptor includes one of a bar code, a magnetic code, a Braille code and machine readable optical characters and the reader includes a matching one of a bar code reader, a magnetic code reader, a Braille code reader and a reader of the optical characters.

27. The apparatus of claim 25 further including a database that correlates each descriptor with associated data to be written to enhanced devices, the processor linked to the database and, when a descriptor is received, identifying by accessing the database and locating the descriptor and associated data.

28. The apparatus of claim 25 wherein the reader includes a hand held device that can be positioned in the vicinity of the descriptor and activated to read the descriptor.

29. The apparatus of claim 28 wherein the hand held device also comprises the writer that can be positioned in the vicinity of the enhanced device and activated to write to the enhanced device.

30. The apparatus of claim 1 further including an enhanced device source that includes the writer and that is linked to the processor wherein, the source provides an enhanced device to an apparatus user for attachment to the container and after the processor identifies the data, the writer writes to the enhanced device.

31. The apparatus of claim 1 wherein the container is a medication container, the data is medication data and the data includes at least a sub-set of a patient ID, the medication type, prescribed dose, recommended dose, a prescribing physician's identification, primary physician's identification and instructions regarding a health safety function.

32. The apparatus of claim 1 wherein descriptors that indicate enhanced data include the enhanced data and the processor identifies by reading the enhanced data.

33. The apparatus of claim 1 wherein each enhanced device is one of a RFID tag, an electronic memory, a magnetic tag, a multi-dimensional bar code and a dot matrix.

34. The apparatus of claim 1 wherein the processor also uses the descriptor to identify human readable indicia to be included on the container wherein the indicia is related to the order, the apparatus further including an indicia printer linked to the processor, the another function including causing the indicia printer to print the human readable indicia for inclusion on the container.

* * * * *